(12) United States Patent
Arnar et al.

(10) Patent No.: US 11,097,110 B2
(45) Date of Patent: Aug. 24, 2021

(54) DELIVERY DEVICE WITH TETHERING FOR IMPLANTABLE MEDICAL DEVICE

(71) Applicant: St. Jude Medical, Cardiology Division, Inc., St. Paul, MN (US)

(72) Inventors: Bernhard Arnar, Minnetrista, MN (US); Steven N. Willard, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 69 days.

(21) Appl. No.: 16/610,553

(22) PCT Filed: Jun. 20, 2018

(86) PCT No.: PCT/US2018/038431
§ 371 (c)(1),
(2) Date: Nov. 4, 2019

(87) PCT Pub. No.: WO2018/236958
PCT Pub. Date: Dec. 27, 2018

(65) Prior Publication Data
US 2020/0101299 A1 Apr. 2, 2020

Related U.S. Application Data

(60) Provisional application No. 62/523,396, filed on Jun. 22, 2017.

(51) Int. Cl.
| | | |
|---|---|---|
| *A61N 1/372* | (2006.01) | |
| *A61N 1/362* | (2006.01) | |
| *A61N 1/375* | (2006.01) | |
| *A61B 17/34* | (2006.01) | |
| *A61N 1/05* | (2006.01) | |
| *A61B 17/00* | (2006.01) | |

(52) U.S. Cl.
CPC ...... *A61N 1/37205* (2013.01); *A61B 17/3439* (2013.01); *A61B 17/3468* (2013.01);
(Continued)

(58) Field of Classification Search
CPC ............ A61N 1/37205; A61N 1/37518; A61N 1/3756; A61B 17/3439; A61B 17/3468;
(Continued)

(56) References Cited

U.S. PATENT DOCUMENTS 8,615,310 B2 12/2013 Khairkhahan et al.
2008/0283066 A1* 11/2008 Delgado ................ A61B 5/076
128/899

(Continued)

FOREIGN PATENT DOCUMENTS

WO 2016/172104 A1 10/2016
WO 2017/074553 A1 5/2017

OTHER PUBLICATIONS

International Search Report—PCT/US2018/038431 (dated Sep. 3, 2018).

*Primary Examiner* — Eric D. Bertram
(74) *Attorney, Agent, or Firm* — Lerner, David, Littenberg, Krumholz & Mentlik, LLP

(57) ABSTRACT

An implantable medical device (402) includes an attachment member (424) having an aperture (428) with a first diameter. A delivery device (400) includes a catheter shaft (406), a tube (450') within the shaft, and a tether (422') within the tube. The tube has a main portion (455') with a second diameter and an expandable distal end (457'). The tether has a body (423') and a tether member (426') having a third diameter greater than the second diameter and smaller than the first diameter. The tether is slideable relative to the tube from a released condition in which the tether member is positioned at least partially distal to the distal end of the tube, and a locked condition in which the tether member is at least partially surrounded by the distal end of the tube. The distal end of the tube can pass through the aperture only in the released condition.

20 Claims, 20 Drawing Sheets

(52) U.S. Cl.
CPC ........... *A61N 1/362* (2013.01); *A61N 1/3756* (2013.01); *A61N 1/37518* (2017.08); *A61B 2017/00243* (2013.01); *A61B 2017/00292* (2013.01); *A61B 2017/347* (2013.01); *A61N 2001/058* (2013.01); *A61N 2001/0578* (2013.01)

(58) Field of Classification Search
CPC ........... A61B 2017/00243; A61B 2017/00292; A61B 2017/347
See application file for complete search history.

(56) References Cited

U.S. PATENT DOCUMENTS

| | | | |
|---|---|---|---|
| 2012/0197373 A1* | 8/2012 | Khairkhahan | A61M 25/0074 607/127 |
| 2014/0074114 A1 | 3/2014 | Khairkhahan et al. | |
| 2016/0067447 A1* | 3/2016 | Paspa | A61N 1/37205 606/129 |
| 2016/0310747 A1* | 10/2016 | Grubac | A61N 1/37512 |
| 2016/0325104 A1* | 11/2016 | Anderson | A61N 1/37518 |
| 2017/0043158 A1* | 2/2017 | Kelly | A61N 1/372 |
| 2017/0095662 A1* | 4/2017 | McDonnell | A61N 1/37205 |
| 2017/0100582 A1* | 4/2017 | McEvoy | A61N 1/3756 |
| 2017/0119999 A1* | 5/2017 | Kelly | A61N 1/37205 |
| 2017/0136231 A1* | 5/2017 | Kelly | A61N 1/0587 |
| 2017/0209688 A1* | 7/2017 | Drake | A61B 5/6882 |
| 2017/0312496 A1* | 11/2017 | Wood | A61B 17/3468 |
| 2018/0028805 A1* | 2/2018 | Anderson | A61B 17/3468 |
| 2018/0318591 A1* | 11/2018 | Kabe | A61N 1/37205 |

\* cited by examiner

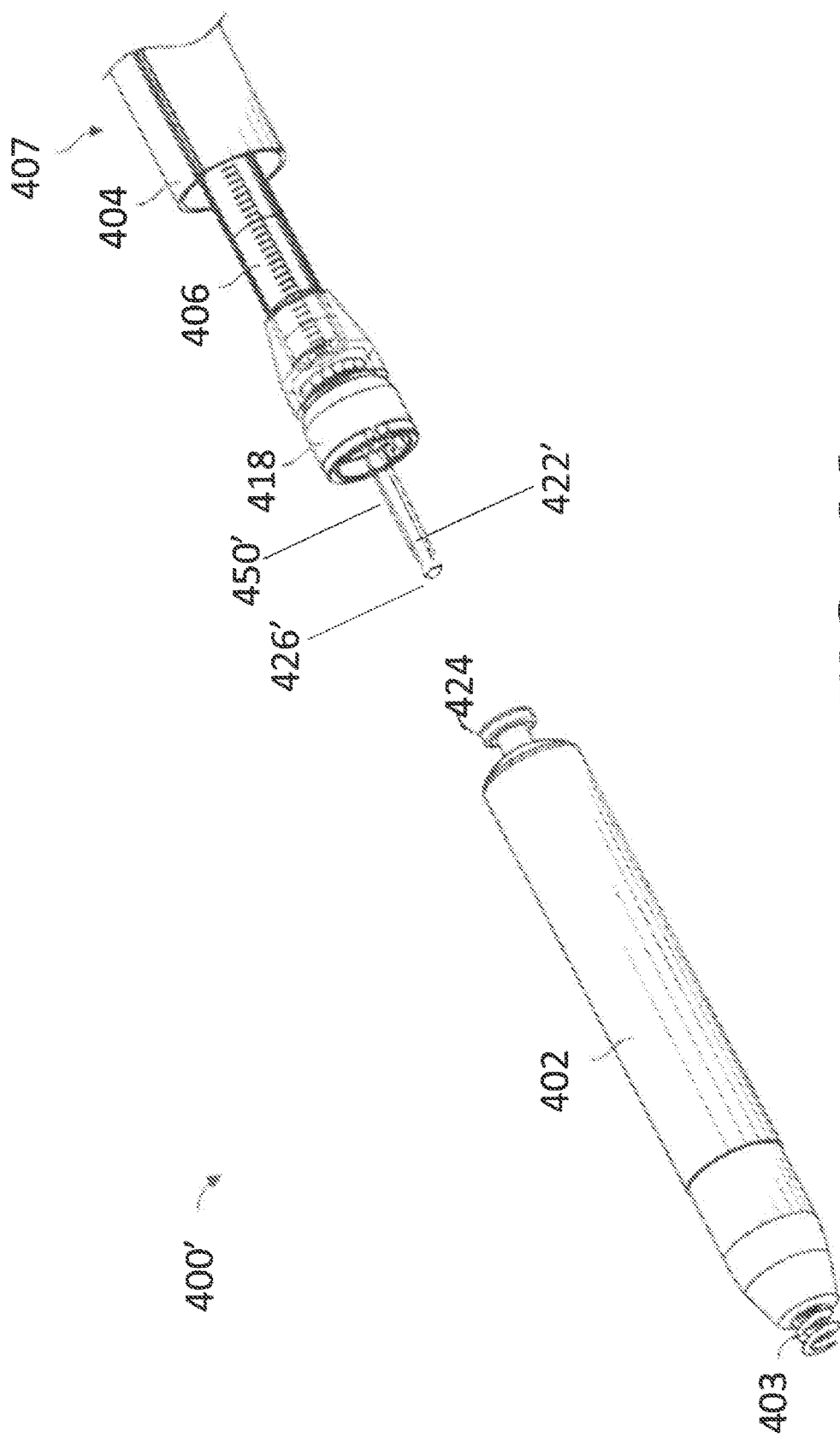

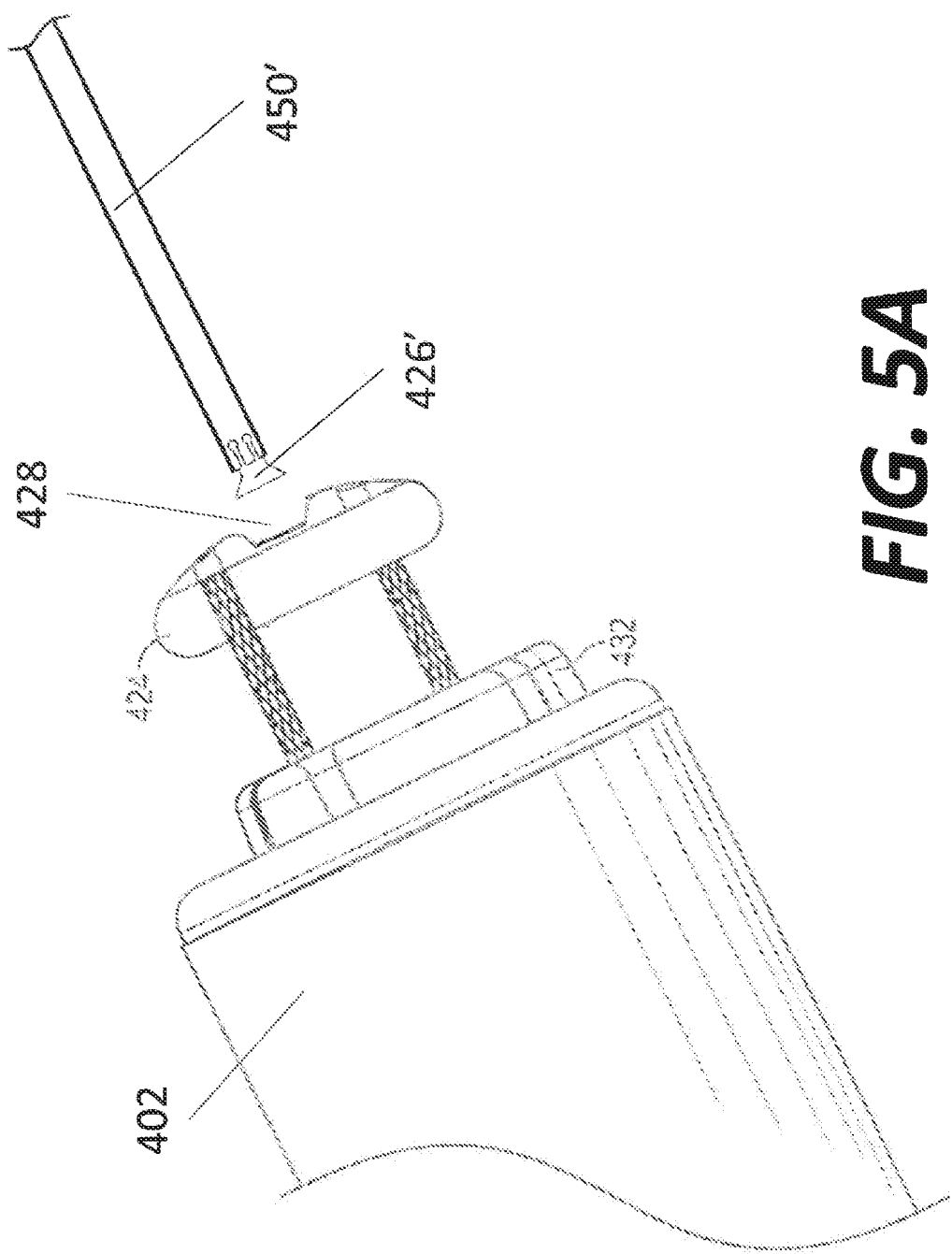

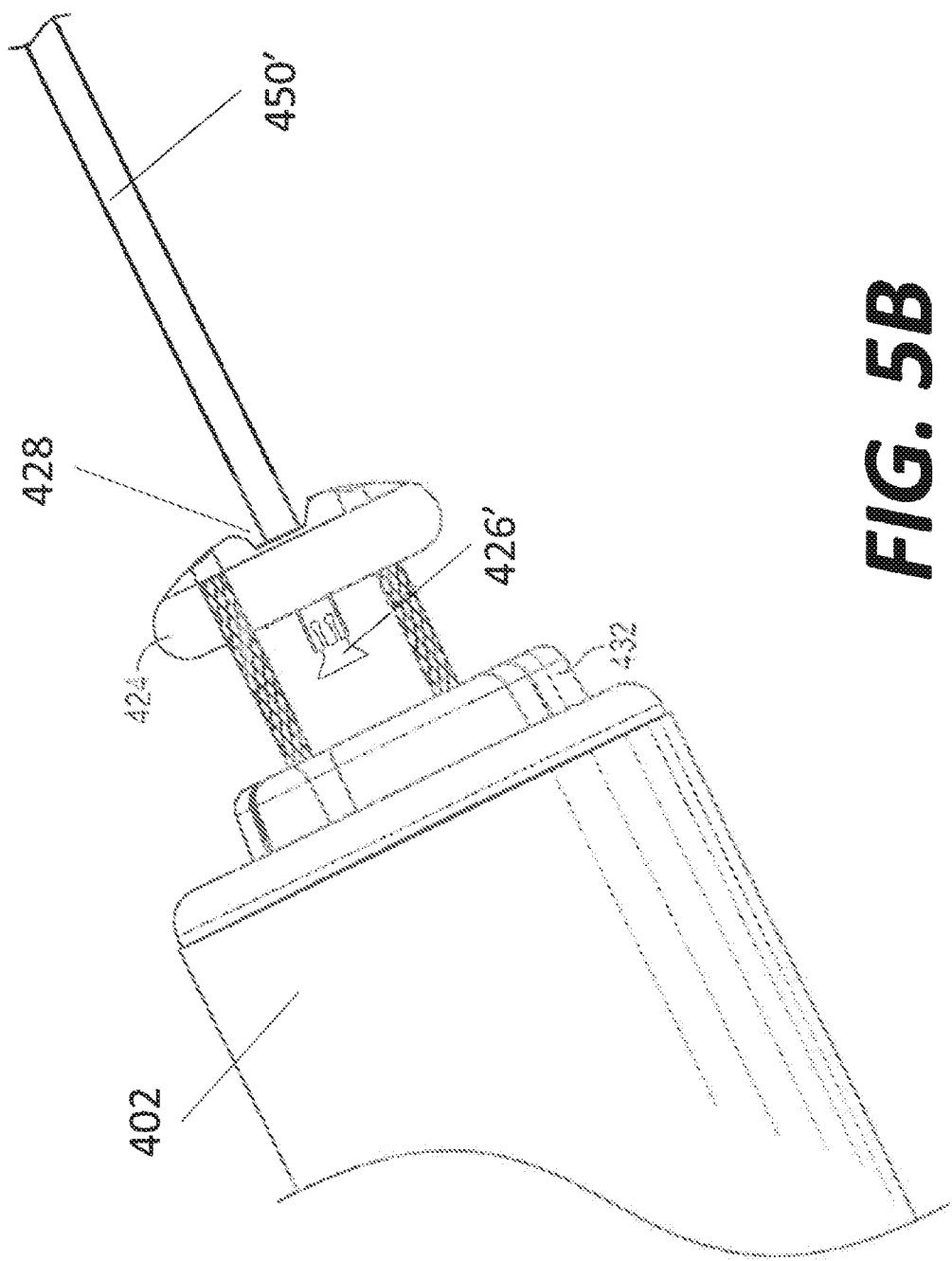

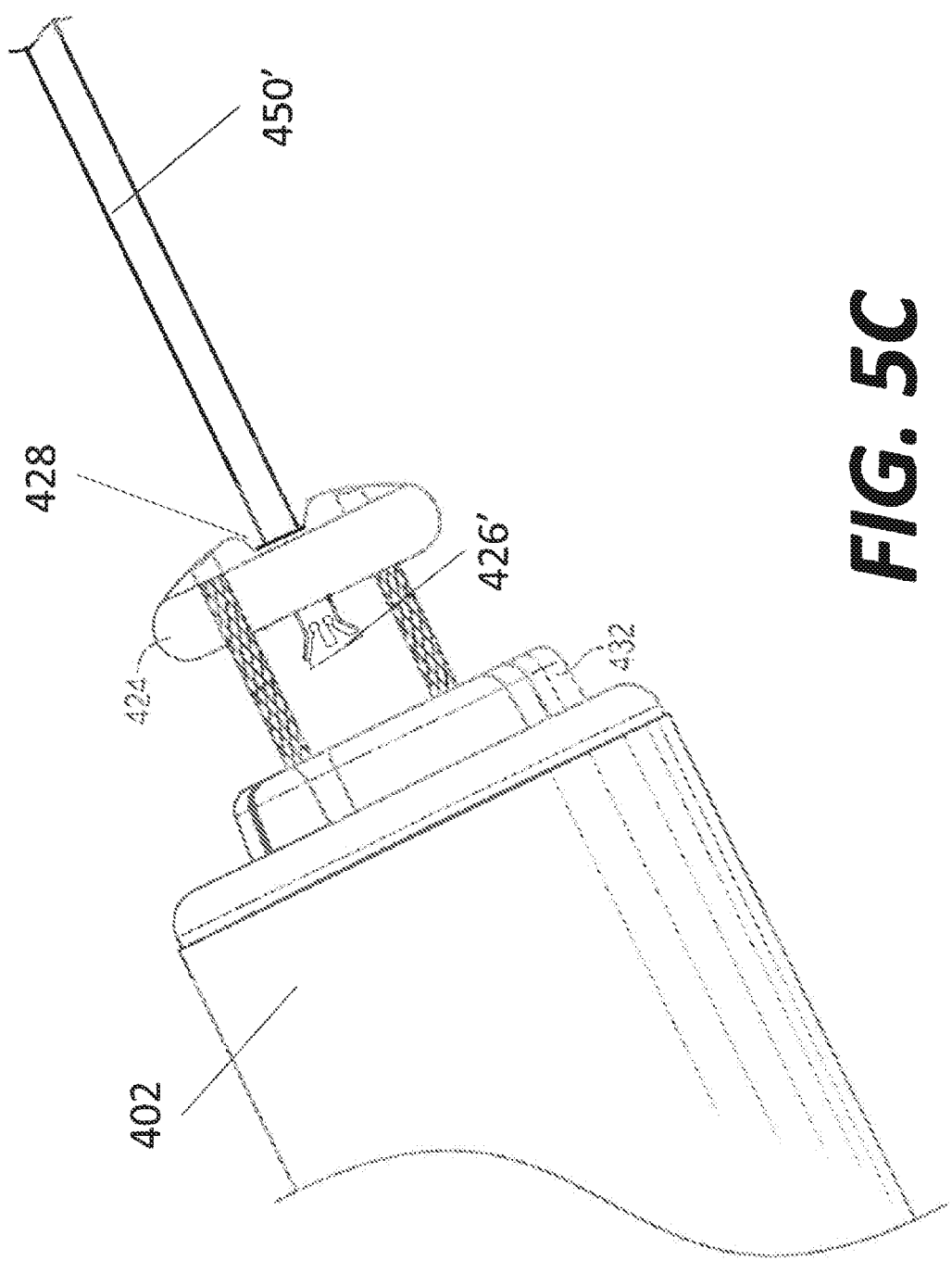

DELIVERY DEVICE WITH TETHERING FOR IMPLANTABLE MEDICAL DEVICE

CROSS-REFERENCE TO RELATED APPLICATIONS

This application is a national phase entry under 35 U.S.C. § 371 of International Application No. PCT/US2018/038431 filed Jun. 20, 2018, published in English, which claims the benefit of the filing date of U.S. Provisional Patent Application No. 62/523,396 filed Jun. 22, 2017, the disclosures of which are hereby incorporated herein by reference.

BACKGROUND OF THE DISCLOSURE

Embodiments of the present disclosure generally relate to implantable medical devices and, more particularly, to systems and methods for implanting a medical device.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Medical devices of this type that are implantable (hereinafter, generally "implantable medical devices" or "IMDs") are configured to be implanted within the patient anatomy and commonly employ one or more leads with electrodes that either receive or deliver voltage, current or other electromagnetic pulses (generally "energy") from or to an organ and/or tissue for diagnostic and/or therapeutic purposes.

Typically, an intra-cardiac IMD is introduced into the heart through a catheter. In general, the IMD may be connected to the catheter in a docked state, in which the IMD is securely attached to the catheter. In the docked state, the catheter may be operated to guide the IMD to an implant site. Once the IMD is proximate to the implant site, the delivery system may be used to torque the IMD into patient tissue.

Once the IMD is secured into patient tissue, the IMD may be moved into a tethered state with respect to the delivery system. In the tethered state, the delivery system separates from the IMD, but remains connected thereto. In one known system and method, two separate and distinct tethers connect the IMD to the catheter in the tethered stated. In the tethered state, an implanting physician may test the IMD to make sure that the IMD is securely and electrically connected to patient tissue at a desired location. If the physical and/or electrical connection between the IMD and the patient tissue is less than optimal, the IMD may be re-docked to the catheter so that the IMD may be moved to a better implanted position.

Once the implanting physician is satisfied with the location of the IMD within the patient anatomy, the IMD is transitioned from the tethered state to a released state. In the released state, the IMD is disconnected from the catheter.

As noted above, in the tethered state, two tethers may connect the IMD to the catheter. Each tether may include a distal tethering member, such as a bump, sphere, stud or the like. The tethering members are typically secured to an attachment feature of the IMD. In order to release the tethers from the attachment feature, the tethers are misaligned with one another so that a combined diameter of the distal ends of the tethers is smaller than a hole formed through the attachment feature. In this manner, both of the tethers may be removed from the attachment feature by sliding them out of the hole.

However, known systems and methods may be susceptible to inadvertent release. That is, the tethers may inadvertently pass through the hole of the attachment feature during implantation before the implanting physician desires to release the IMD from the catheter. For example, if the IMD in the tethered state moves out of axial alignment with a distal end of the catheter, the two tethers may become staggered with respect to one another as the tethering lines splay away from one another. As a result, the tethering members at the distal ends of the tethering lines may misalign with one another, and the tension within the tethering lines may cause the tethering members to retreat out of the hole within the attachment feature, thereby releasing the IMD from the catheter. As such, the IMD may be inadvertently released from the catheter when an implanting physician still desires to test the IMD in a tethered state. Also, the tethers may become entangled with one another, making it difficult to transition the IMD to the released state.

BRIEF SUMMARY

According to a first aspect of the disclosure, a delivery system is for delivering an implantable medical device having an aperture with a first diameter. The delivery system includes a catheter shaft having a distal end, and a tube disposed within the catheter shaft. The tube has a main portion with a second diameter, a distal end and an expandable distal end portion extending distally beyond the distal end of the catheter shaft. A tether is disposed within the tube. The tether includes an elongated body having a distal end and a tether member at the distal end of the body. The tether member has a third diameter greater than the second diameter and smaller than the first diameter. The tether is slideable relative to the tube from a released condition in which the tether member is positioned at least partially distal to the distal end of the tube, and a locked condition in which the tether member is at least partially surrounded by the expandable distal end portion of the tube. In the released condition, the distal end of the tube has a diameter smaller than the first diameter, and in the locked condition, the distal end of the tube has a diameter larger than the first diameter.

Another aspect of the disclosure is directed to a method of implanting a medical device in a patient, the medical device having an aperture with a first diameter. The method includes providing a delivery device having a catheter shaft with a distal end, a tube disposed within the catheter shaft, and a tether disposed within the tube. The tube and tether are advanced distally through the aperture while the tube is in a released condition in which a distal end of the tube has a diameter smaller than the first diameter. The tether is retracted proximally relative to the tube to transition the tube to a locked condition in which the distal end of the tube has a diameter larger than the first diameter. The medical device is provisionally implanted into the patient while the tube is in the locked condition. The delivery device is removed from the patient.

BRIEF DESCRIPTION OF THE DRAWINGS

FIG. 4A is a perspective view of the distal end of a delivery catheter disconnected from an IMD, according to an aspect of the present disclosure.

FIGS. 5A-C are perspective views illustrating the coupling of the delivery catheter of FIG. 4A to an IMD.

DETAILED DESCRIPTION

As used herein, the term "proximal" refers to a point nearer a user of a device being inserted into a patient (the trailing end) whereas the term "distal" refers to a point farther away from the user of the device (the leading end) when the device is being used as intended.

Figure 1:
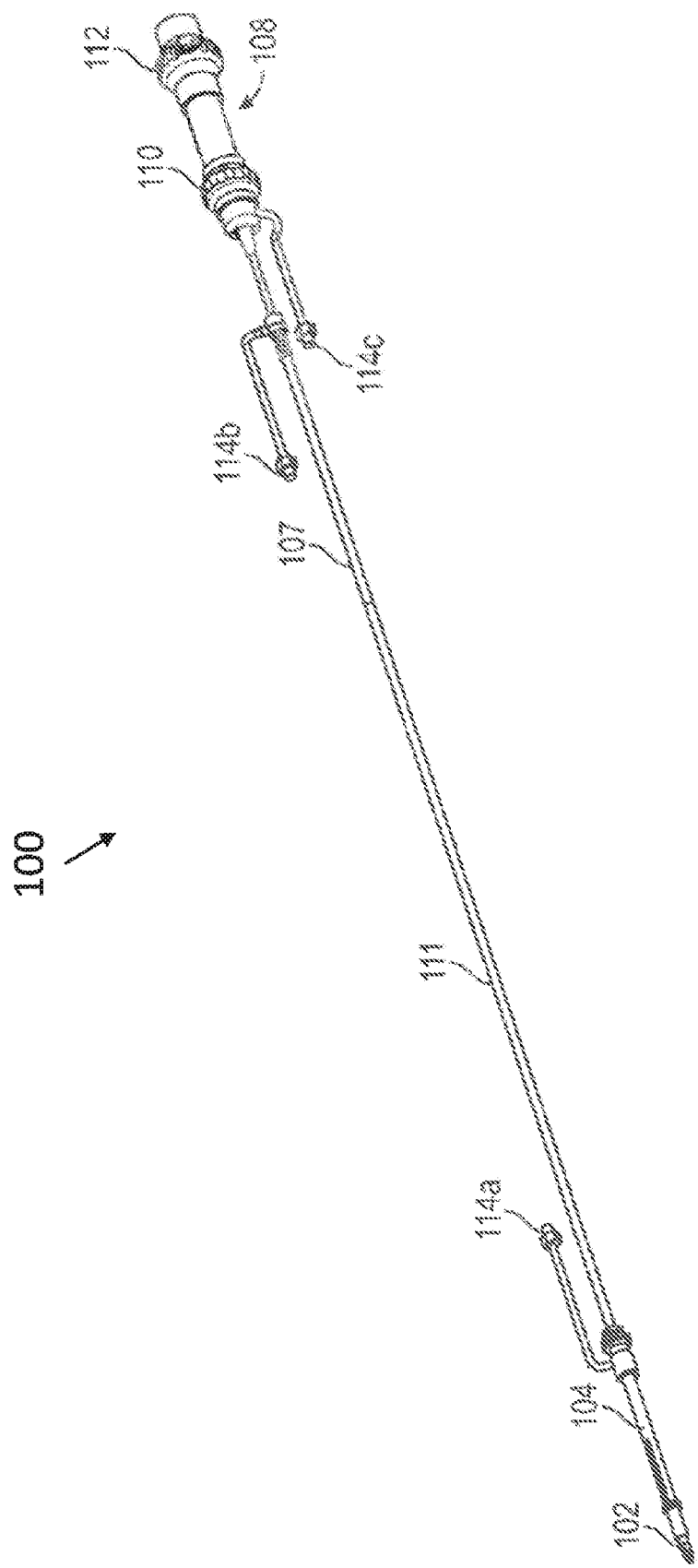
FIG. 1 is a perspective view of a delivery system for delivering an implantable medical device (IMD) into a patient, according to the prior art.

FIG. 1 illustrates a perspective view of a delivery system 100 for delivering an IMD 102 into a patient, according to the prior art. The delivery system 100 may include an IMD sheath 104, a guide catheter 111, an introducer sheath 107, a handle 108, a deflection knob 110, a tether shuttle 112, and flush ports 114a, 114b, and 114c. The deflection knob 110 may be used in a known fashion to steer and guide the catheter 111 during implantation and/or removal of the IMD 102. The flush ports 114a, 114b, and 114c may be used to flush saline or other fluids through the catheter 111. The introducer sheath 107 may be advanced distally over the catheter 111 to provide additional steering and support for the catheter during implantation and to surround the IMD 102 as it is introduced through a trocar or introducer into a patient. Additional information relating to delivery system 100 may be found in U.S. Pat. No. 8,615,310 and U.S. Patent Publication No. 2016/0067447, the disclosures of which are both hereby incorporated by reference herein.

Figure 2A:
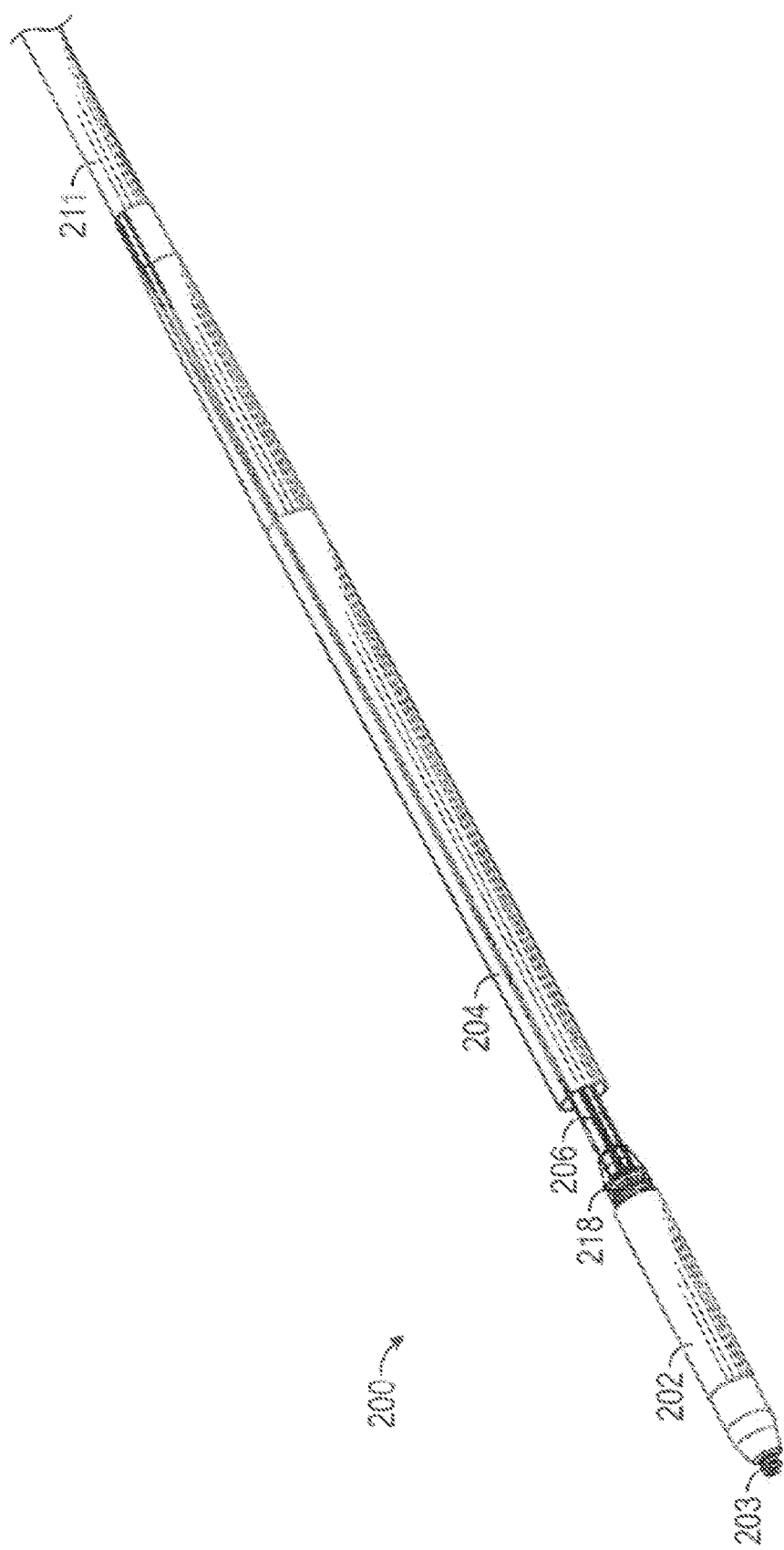
FIG. 2A is a perspective view of a distal portion of a delivery system and an IMD, according to the prior art.

FIG. 2A is a perspective view of the distal portion of a delivery system 200 and an IMD 202, according to the prior art. Delivery system 200 includes a catheter 206 and a guide shaft 211, as well as an IMD sheath 204 that is slidable relative to the catheter and the guide shaft. The IMD 202 may include a corkscrew wire or helix 203 that may be used to attach the IMD 202 to the tissue of a patient. The IMD 202 may include an attachment member that is configured to removably connect to a docking cap 218 of the catheter 206. As shown in the figure, IMD sheath 204 is pulled back proximally along the catheter 206 and the guide shaft 211 to expose the IMD 202 and the helix 203.

Figure 2B:
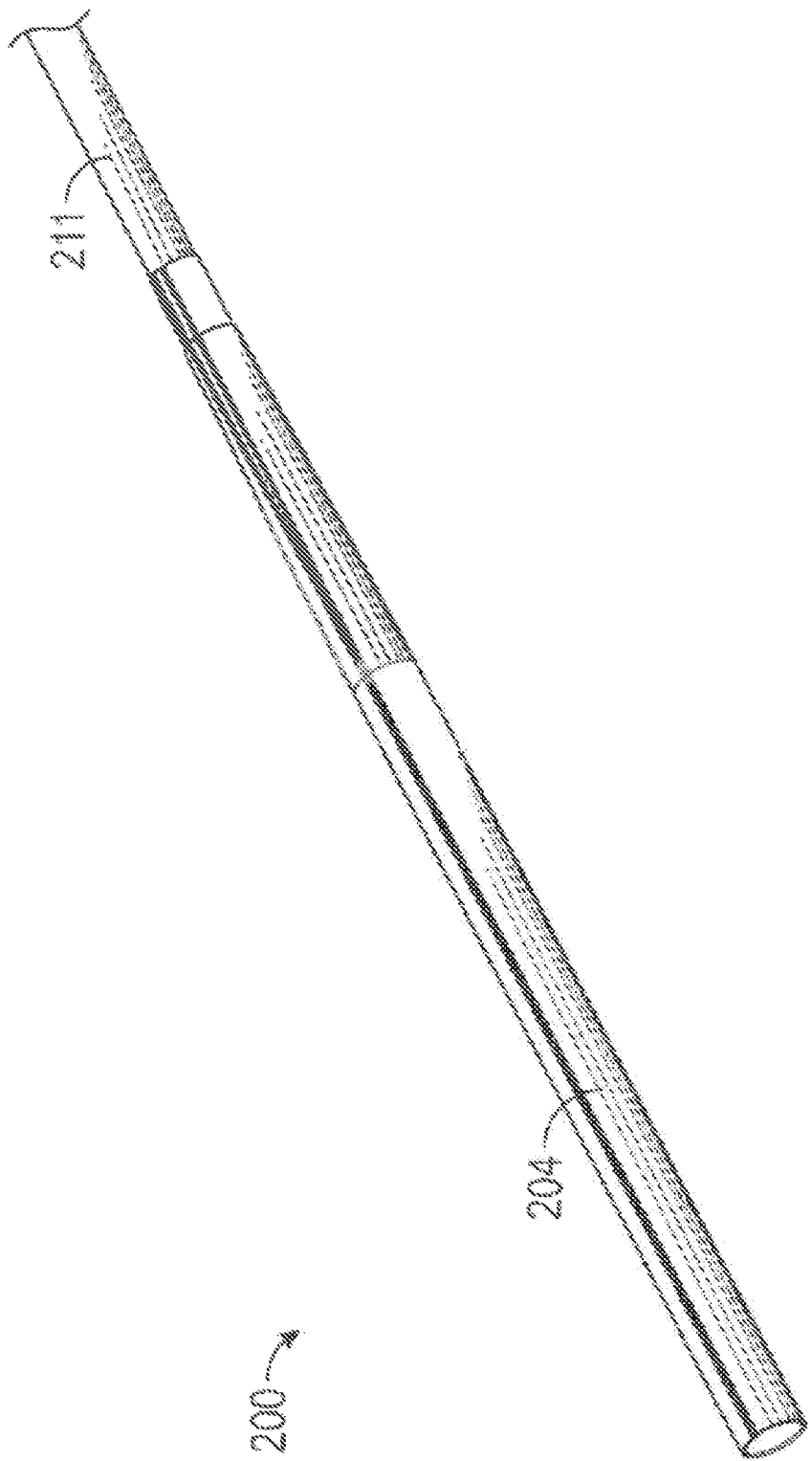
FIG. 2B is a perspective view of an IMD sheath extended distally along a guide shaft in the delivery system of FIG. 2A.

FIG. 2B is a perspective view of the IMD sheath 204 extended distally along the guide shaft 211 to cover the catheter 206, the IMD 202, and the helix 203. The extended IMD sheath 204 protects patient tissue from sharp edges of the helix 203 during implantation. When the IMD sheath 204 is pulled back proximally, as shown in FIG. 2A, the IMD 202 is in an exposed, delivery configuration. When the IMD sheath 204 is advanced distally to protect the IMD 202 and the helix 203, as shown in FIG. 2B, the IMD 202 is in a protected, advancement configuration.

Figure 3A:
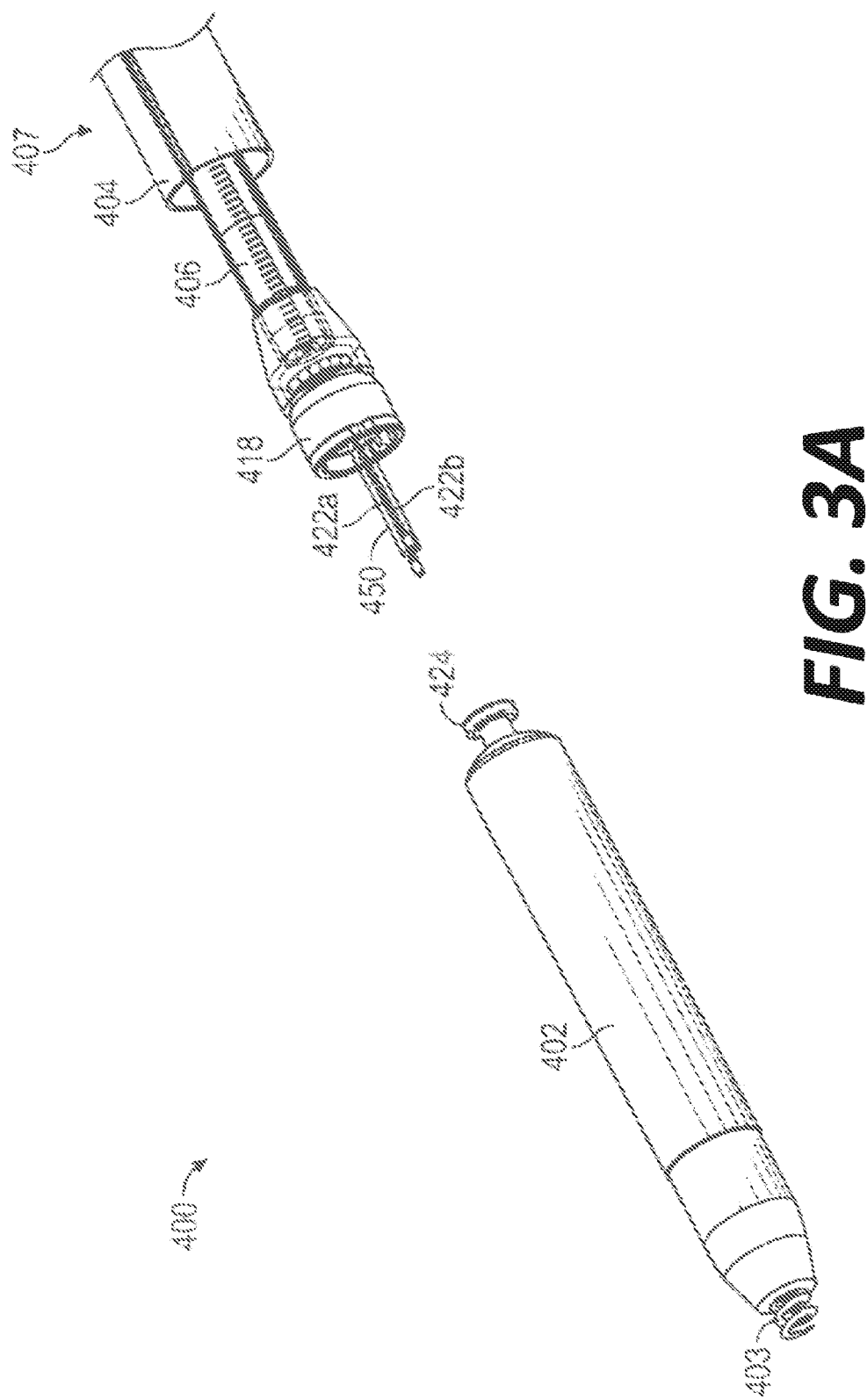
FIG. 3A is a perspective view of the distal end of a delivery catheter disconnected from an IMD, according to the prior art.

FIG. 3A is a perspective view of the distal portion of a delivery system 400 disconnected from an IMD 402, according to the prior art. The IMD 402 may include a helix 403 and an attachment member 424, such as a docking button, cap, stud, ridge, ledge, rim or the like. Delivery system 400 may include components described in relation to delivery system 100, for example including a handle, a deflection knob, a tether shuttle, and flush ports.

The delivery system 400 includes a delivery catheter 407 that may include an IMD sheath 404, a catheter shaft 406, a docking cap 418, tethers 422a and 422b, and a restrainer 450 that extends outwardly from the catheter shaft 406 and surrounds at least portions of the tethers 422a and 422b. The restrainer 450 may be or may include a flexible tube, lumen, cable, shaft, sleeve, sheath, or the like having an outer circumferential wall surrounding an interior passage into which at least portions of the tethers 422a and 422b may be retained.

Each tether 422a and 422b may include a tethering line and a tether member at the distal end of the tether line. Thus, tether 422a may include a tether line 424a and a tether member 426a at the distal end of the tether line. Similarly, tether 422b may include a tether line 424b and a tether member 426b at the distal end of the tether line. Tethering lines 424a and 424b may include wires, shafts, tubes, cords, ropes, strings, or other similar structures that may extend through the length of the restrainer 450, which, in turn, may extend through the catheter shaft 406. In at least one embodiment, the tethering lines 424a and 424b may include a shape memory material, including nickel titanium alloys such as nitinol. In other embodiments, the tethering lines 424a and 424b may include stainless steel wires or braids. As shown in FIG. 3A, the IMD 402 is disconnected from the docking cap 418 of the delivery catheter 407. Preferably, although flexible, tethers 422a, 422b are rigid enough so that they may be advanced distally by pushing the wires in a distal direction.

Figure 3B:
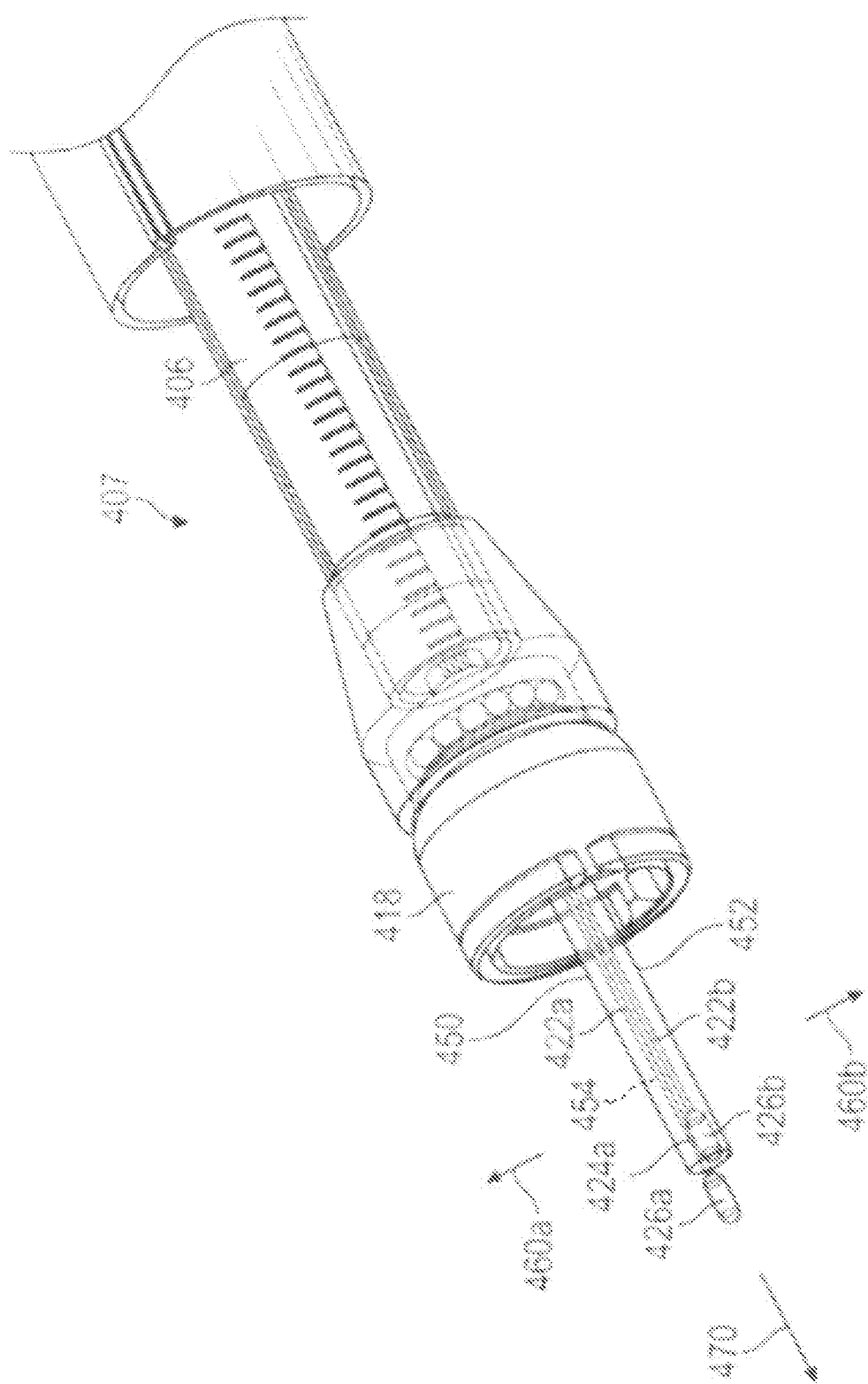
FIG. 3B is an enlarged perspective view of the distal end of the delivery catheter of FIG. 3A with misaligned tethering members, according to the prior art.
Figure 3C:
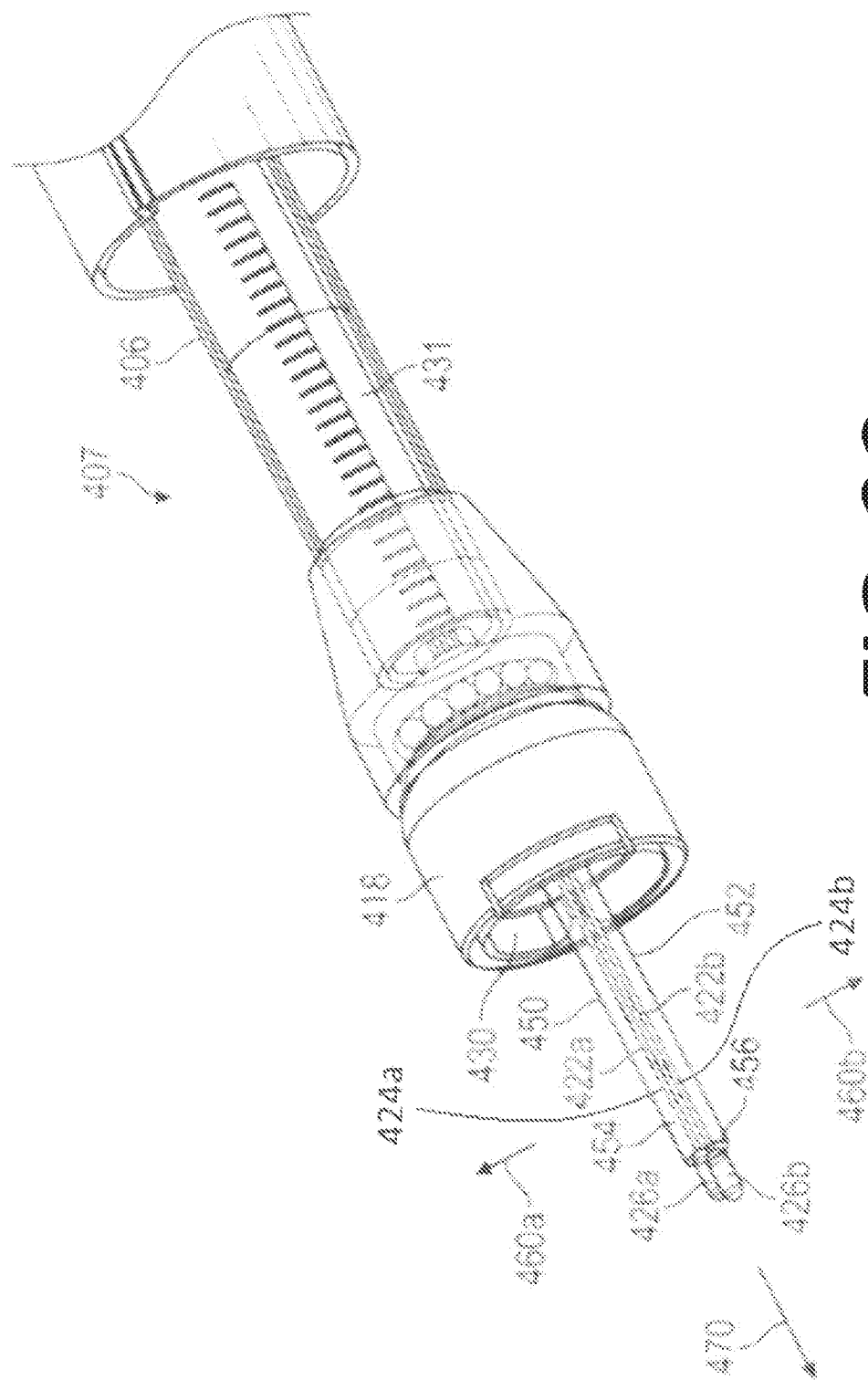
FIG. 3C is an enlarged perspective view of the distal end of the delivery catheter of FIG. 3A with aligned tethering members.

FIG. 3B is an enlarged perspective view of the distal end of the delivery catheter 407 with misaligned or unaligned tethering members 426a and 426b. FIG. 3C is a perspective view of the distal end of the delivery catheter 407 in which the tethering members 426a and 426b are aligned. Referring to FIGS. 3B and 3C, the tethers 422a and 422b may include the tethering members 426a and 426b at their distal ends. For example, the tethering members 426a and 426b may be or may include features on the tethering lines 424a and 424h that protrude radially from their distal ends, such as bumps, spheres, cylinders, blocks, or other shapes that extend outwards from the tethering lines 424a and 424b. In at least one embodiment, each tethering member 426a and 426b may be an expandable element, such as a balloon, or other expandable mechanical structure. In general, the tethering members 426a and 426b may each have a transverse cross-section that is larger than the transverse cross-section of the tethering lines 424a and 424b. In at least one embodiment, tether 422a may be advanced further from the catheter 407 than tether 422b (as shown in FIG. 3B), so that when the tethers 422a and 422b are pushed together, the tethering member 426b is positioned behind tethering member 426a and rests against the tethering line 424a. As such, the combined transverse cross-section of both tethering members 426a and 426b and tethering lines 424a and 424b may be less than if the tethering members were lined up side-by-side. The tethering members 426a and 426b may be configured to be moved between an aligned side-by-side configuration (as shown in FIG. 3C), and a misaligned or unaligned configuration (as shown in FIG. 3B).

In order to connect the delivery catheter 407 to the IMD 402, the lengths of tethers 422a and 422b, and thus the positions of tethering members 426a and 426b, may be adjusted so that the tethering members 426a and 426b are not aligned in a side-by-side configuration.

As shown in FIGS. 3B and 3C, in particular, the restrainer 450 includes a flexible elongated body 452, such as a tube, that defines an internal passage 454 terminating in an opening 456 at the distal end 462 of body 452. The interior diameter of the internal passage 454 and the opening 456 may be greater than the combined transverse cross-section of the tethering members 426a and 426b in an aligned configuration. Alternatively, the interior diameter of the internal passage 454 may only be large enough to contain the tethering members in a misaligned or unaligned configuration, e.g., with tethering member 426b positioned behind tethering member 426a and next to tethering line 424a (or vice versa). In the aligned condition, both of the tethering members 426a and 426b may be fully extended out of the distal opening 456 of the restrainer 450, as shown in FIG. 3C.

The restrainer 450 restrains, constricts, or otherwise limits outward bowing, flexing, splaying, or other such movement of the tethers 422a and 422b away from one another in the directions of arrows 460a and 460b. For example, the restrainer 450 limits the movement of tether 422a away from tether 422b in the direction of arrow 460a and the movement of tether 422b away from tether 422a in the direction of arrow 460b. As such, the restrainer 450 maintains the tethers 422a and 422b in close proximity to one another such that the tethers remain generally aligned (such as being parallel) with an advancement or tethering direction 470 of the delivery catheter 407. Accordingly, the restrainer 450 protects against, or otherwise reduces the possibility of, the tethers 422a and 422b inadvertently releasing from the attachment member 424 of the MID 402 (shown in FIG. 3A, for example).

The restrainer 450 may compress, squeeze, or otherwise force the tethers 422a and 422b together so that there is little or no clearance, gap, or the like between them. As such, the restrainer 450 may be formed of a resilient material, such as an elastomeric material, that exerts a compressive force on the tethers 422a and 422b. Alternatively, the restrainer 450 may define a central passage 454 having a constant diameter throughout that allows the tethers 422a and 422b to move toward and away from each other over short distances. The outer wall of body 452 limits such movement. For example, the diametric clearance within the central passage 454 may be less than the diameter of a tethering member 426a or 426b.

The forces exerted on the tethers 422a and 422b by the restrainer 450 may keep the tethers aligned along a similar track, path, or the like. As such, the outstretched length of the tethers 422a and 422b relative to one another may remain constant (or substantially constant). The restrainer 450 minimizes or otherwise reduces tether splaying or separation during device deployment and implantation.

For the sake of clarity, the restrainer 450 is shown in the figures as being translucent, so that the tethers 422a and 422b are visible. However, it is to be understood that the restrainer 450 may be shaded, opaque, or various colors, tints, hues, and the like.

Figure 3D:
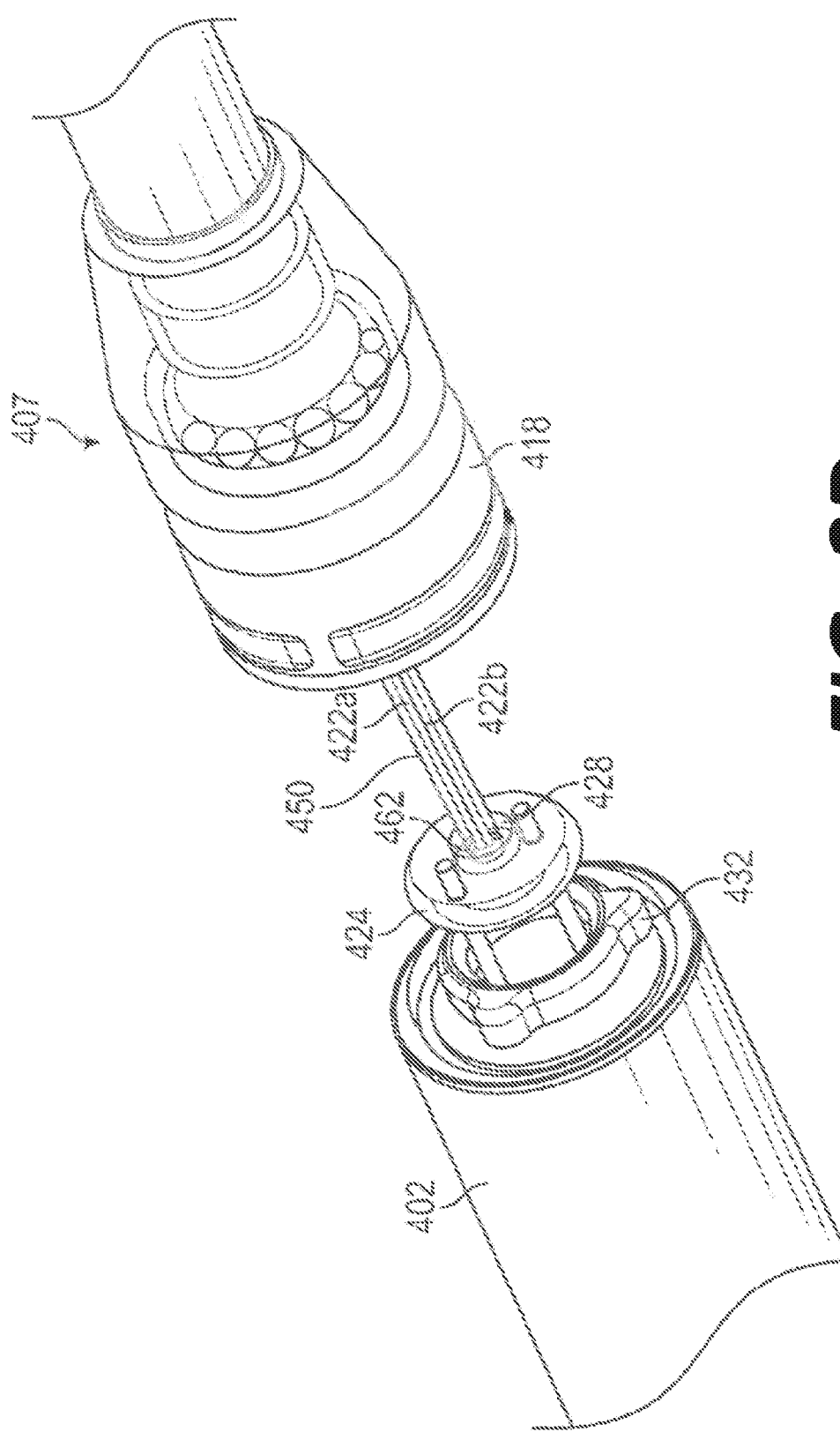
FIG. 3D is an enlarged perspective view of the distal end of the delivery catheter of FIG. 3A tethered to an IMD, according to the prior art.
Figure 3E:
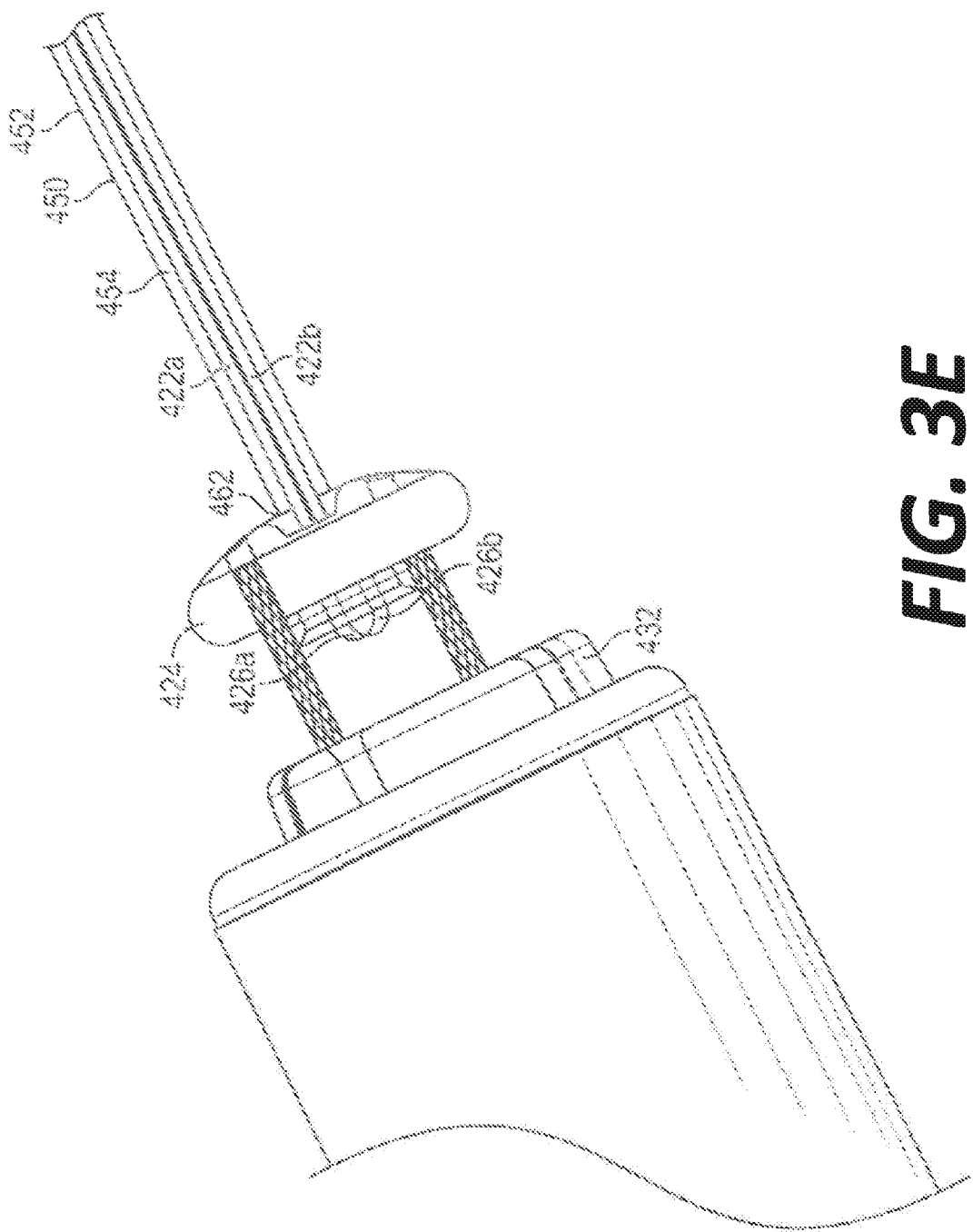
FIG. 3E is a lateral view of the delivery catheter of FIG. 3A tethered to an IMD.

FIG. 3D is a perspective view of the delivery catheter 407 coupled by tethers 422a and 422b. FIG. 3E is a lateral view of the delivery catheter 407 connected to the IMD 402 by the tethers. Referring to FIGS. 3D and 3E, the tethering members 426a and 426b may be advanced into and through an aperture 428 in the attachment member 424 of IMD 402. The diameter of aperture 428 is large enough to allow the tethering members 426a and 426b of the tethers 422a and 422b, respectively, to pass through when in the misaligned configuration (as shown in FIGS. 3A and 3B). Once the tethering members 426a and 426b have passed through aperture 428, the length of the tethers 422a and 422b may be adjusted to align the tethering members 426a and 426b in the side-by-side configuration. In this state, the combined transverse cross-section of the tethering members 426a and 426b is larger than the diameter of aperture 428, thereby locking the tethers 422a and 422b and tethering members 426a and 426b in the attachment member 424.

The distal end 462 of the restrainer 450 may not extend into aperture 428. Instead, the aligned tethering members 426a and 426b may extend outwardly in the longitudinal direction of the restrainer 450 from the opening 456 at the distal end of body 452, while the distal end 462 of the restrainer 450 may abut the outer surface of the attachment member 424 surrounding the hole 428. Optionally, the distal end 462 of the restrainer 450 may be sized and shaped to also fit into aperture 428. For example, the distal end 462 of the restrainer 450 may pass into the aperture 428, while the aligned tethering members 426a and 426b extend outwardly in the longitudinal direction from the opening 456.

The docking cap 418 of the delivery catheter 407 may include a recess 430 that is sized and configured to mate with a torque key 432 located on a proximal end of the IMD 402. The docking cap 418 may be operatively coupled to a torque shaft (not shown), which may extend the length of the delivery catheter to a handle (not shown). The torque key 432 may have a "male" configuration for mating with the recess 430. Alternatively, torque key 432 may be provided on docking cap 418, and recess 430 in docking cap 418 may be provided on the IMD 402. The torque key 432 and recess 430 may be formed with any number of shapes, such as a square, rectangle, triangle, pentagon, hexagon, cross, "X", and the like, so long as the key fits within the recess and can transfer rotational torque from the torque shaft to the IMD 402. Once the tethers 422a and 422b are locked within the attachment member 424, pulling the tethers proximally will draw the IMD 402 towards and into engagement with the delivery catheter 407, thereby engaging the torque slot with the torque key 432 with the recess 430 in the docking cap 418.

As described above, the tethers 422a and 422b may be used to couple the IMD 402 to the delivery catheter 407. To decouple tethers 422a and 422b from the IMD 402, the tethers may be misaligned with respect to one another so that the tethering members 426a and 426b again fit through the aperture 428 in the attachment member 424. Once misaligned, the tethers 422a and 422b may be removed from the attachment member 424 to release the IMD 402 from the delivery catheter 407. The coupling of the IMD 402 to and decoupling of the IMD from the delivery catheter 407 is further described in United States Patent Application Publication No. 2014/0074114, entitled "Delivery Catheter Systems and Methods," the disclosure of which is hereby incorporated by reference herein.

There are at least two potential drawbacks to the tethering system described above. First, having two tethers 422a and 422b extend the entire length of delivery catheter 407 may require considerable space in a system in which it is desirable to minimize size. Second, tethers 422a and 422b may become unintentionally misaligned, for example as portions of the delivery catheter 407 flex as the delivery catheter is advanced through a tortuous anatomy, which may result in an unintended release of the IMD 402 from the delivery catheter.

Figure 4B:
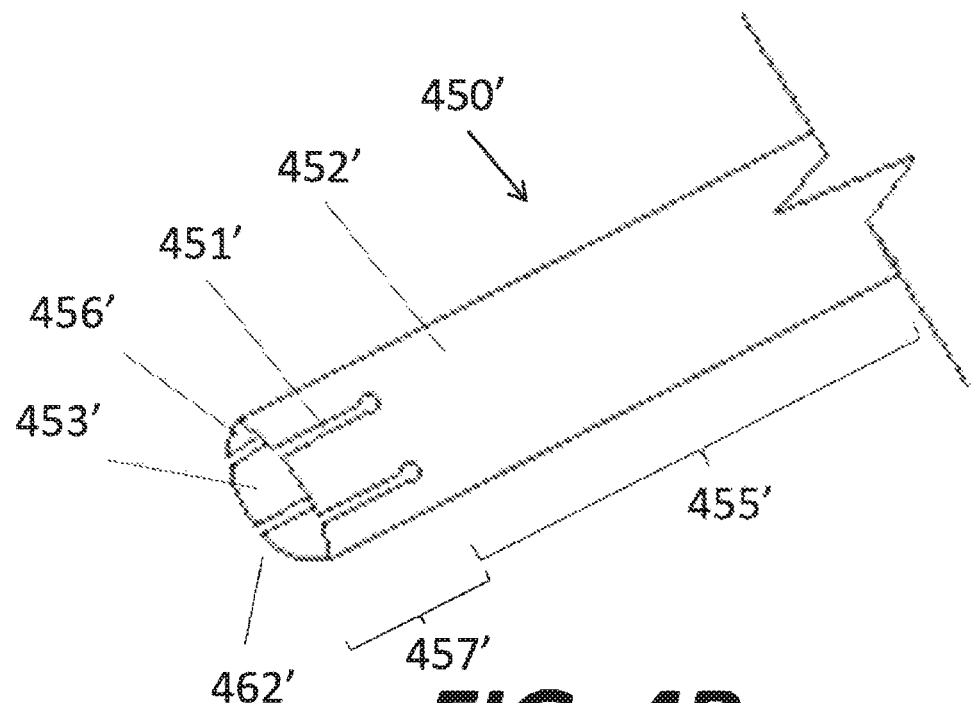
FIG. 4B is a perspective view of the distal end of a tube of the delivery catheter of FIG. 4A.

FIG. 4A is a perspective view of a delivery system 400' according to the present disclosure, disconnected from IMD 402. Delivery system 400' may help mitigate at least some of the drawbacks of the delivery system described above. It should be understood that components of delivery system 400' may be identical or substantially identical to components of the previously described delivery system, with the exceptions described below. For example, delivery system 400' may include components described in relation to delivery system 100, for example including a handle, a deflection knob, a tether shuttle, and flush ports Delivery system 400' has a tethering system that includes a tube 450' extending through catheter shaft 406 and distally beyond a docking cap 418 at the distal end of catheter shaft 406. A tether 422' extends through tube 450'. FIG. 4B is a perspective view of tube 450' isolated from other components of delivery system 400'. Tube 450' may have a flexible elongated body 452' with an opening 456' at the distal end 462' thereof. A plurality of slits 451' are formed in body 452', each slit 451' extending substantially parallel to the longitudinal axis of the body from the distal end 462' of the body proximally by a predetermined distance. Slits 451' may be formed by laser cutting tube 450' or by any other suitable method. In the illustrated embodiment, four slits 451' are shown. In other embodiment, body 452' may include as few as two slits 451', three slits, or more than four slits. Slits 451' are preferably spaced at substantially equal intervals around the circumference of body 452'. With this configuration, the opening 456' is defined by a substantially circular rim at the distal end 462' of body 452', with the rim interrupted along its periphery by slits 451'.

Slits 452' define a plurality of flanges 453' in the distal end 462' of body 452', each flange being formed between circumferentially adjacent slits 451'. The slits 451' enable the flanges 453' to expand radially outwardly relative to the remainder of body 452'. In other words, body 452' may include a static diameter portion 455' and a variable diameter portion 457' defined by flanges 453'. Still referring to FIG. 4B, it should be understood that static diameter portion 455' may extend from the closed ends of slits 451' proximally along the entire length of body 452'. When no force is applied to the flanges 453', the static diameter portion 455' and the variable diameter portion 457' may have substantially equal diameters. This rest condition may be achieved based on the geometry and/or material properties of tube 450', which may include forming tube 450' from a shape memory material such as nitinol. However, if a radially outward force is applied to flanges 453', the flanges may flex radially outward to an expanded condition in which variable diameter portion 457' has a greater diameter than static diameter portion 455'. It should be understood that, because flanges 453' may flex outwardly in a hinged fashion, in the expanded condition, variable diameter portion 457' may actually have a substantially conical or frustoconical shape, resulting in a plurality of different diameters, each greater than the diameter of static diameter portion 455'.

Figure 4C:
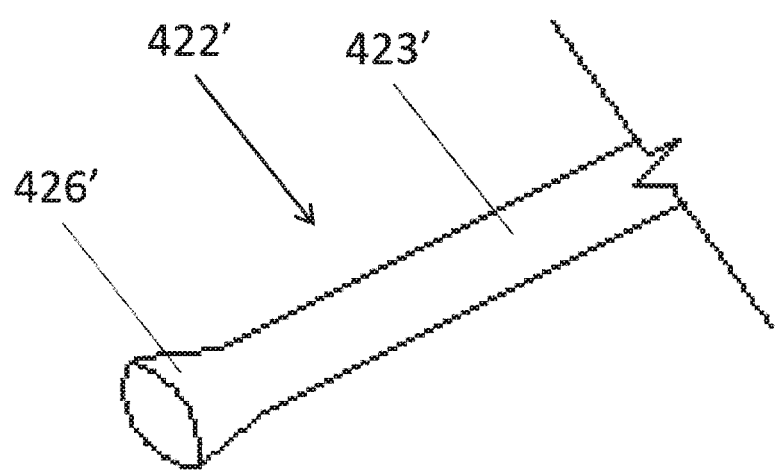
FIG. 4C is a perspective view of the distal end of a tether of the delivery catheter of FIG. 4A.

FIG. 4C is a perspective view of tether 422' isolated from other components of delivery system 400'. Tether 422' may be substantially similar to tethers 422a and/or 422b. For example, tether 422' may be a wire or similar structure, and may include a substantially cylindrical portion 423' extending a majority of the length of the tether, and may terminate at the distal end of the cylindrical portion in an enlarged tethering member 426'. In the illustrated embodiment, tethering member 426' has a substantially conical or frustoconical shape, with the diameter of the tethering member increasing from an area of attachment to cylindrical portion 423' toward a free end of the tethering member. The substantially cylindrical portion 423' of tether 422' has a diameter that is less than the inner diameter of the static diameter portion 455' of body 452'. However, as it tapers outwardly, the diameter of a tethering member 426' gradually increases to diameters that are larger than the inner diameter of the static diameter portion 455' of body 452'. Preferably, at least half the length of tethering member 426' has diameters that are larger than the inner diameter of the static diameter portion 455'.

Figure 4D:
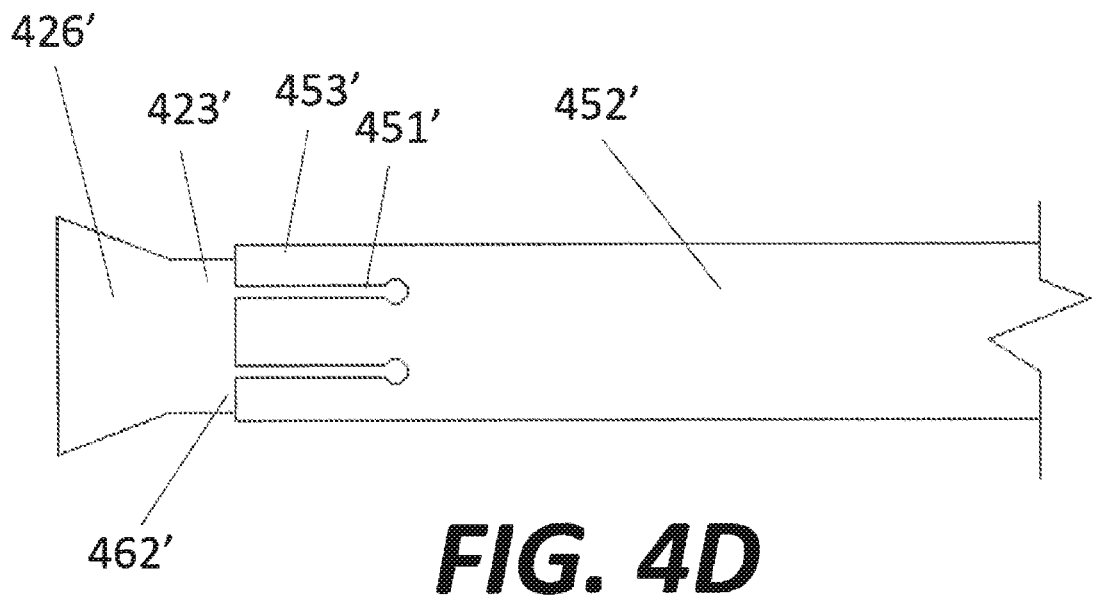
FIG. 4D is a side view of the distal end of the tube of FIG. 4B assembled to the tether of FIG. 4C in a released condition.
Figure 4E:
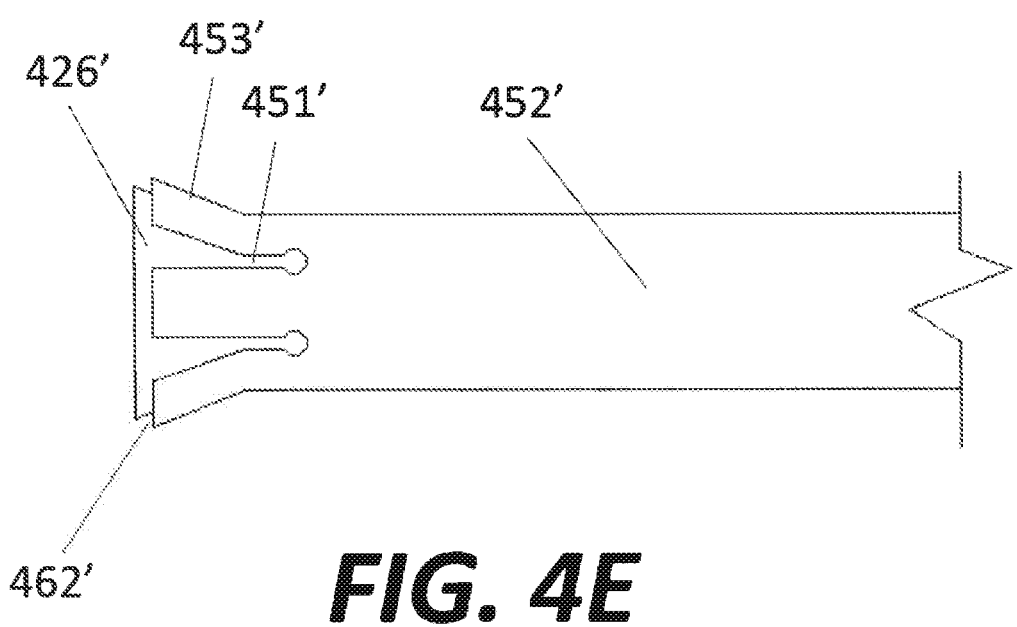
FIG. 4E is a side view of the distal end of the tube of FIG. 4B assembled to the tether of FIG. 4C in a locked condition.
Figure 4F:
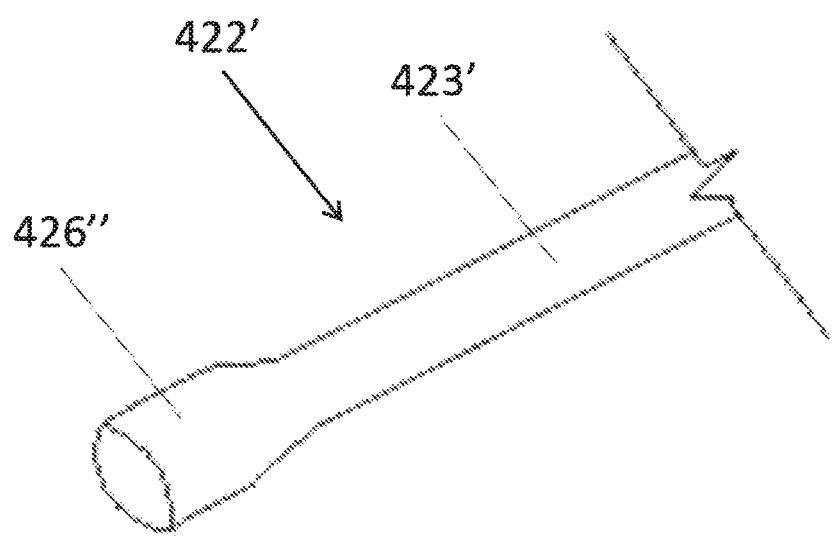
FIG. 4F is a perspective view of the distal end of an alternate tether for use with the delivery catheter of FIG. 4A.

FIG. 4D is a side view of tether 422' assembled within tube 450' in a released condition. In the released condition, cylindrical portion 423' extends beyond the distal end 462' of tube 450'. In other words, in the released condition, the tethering member 426' is positioned entirely or substantially entirely distal to the distal end 462' of tube 450' so that flanges 453' are in the rest condition. Tether 422' may be pulled proximally with respect to tube 450' until tethering member 426' enters the opening 456' of tube 450'. As it moves proximally into opening 456', the tapered shape of tethering member 426' will cause flanges 453' to flex radially outwardly to an expanded condition until tether 422' is placed in the locked condition shown in FIG. 4E. In the locked condition, flanges 453' overlie portions of the outer surface of tethering member 426' and the distal end of the assembled tube 450' and tether 422' has a diameter larger than the largest diameter of tethering member 426'. In other words, the thickness of the flanges 453' that overlie tethering member 426' result in a total diameter that is larger than the distalmost end of the tethering member. In another embodiment, shown in FIG. 4F, tethering member 426" includes a proximal conical portion that transitions into a distal cylindrical portion, providing a generally similar function as tethering member 426'.

FIGS. 5A-C show the steps taken to couple tube 450' and tether 422' to IMD 402. To begin, as shown in FIG. 5A, the tube and tether assembly is placed in the released condition and positioned adjacent to the attachment member 424 of the IMD. The diameter of the aperture 428 in attachment member 424 is only slightly larger than the largest diameter of tether member 426'. While in the released condition, the tube 450' and tether 422' assembly may be inserted through the aperture 428 in attachment member 424 until the flanges 453' are partially or entirely positioned beyond the aperture 428, as shown in FIG. 5B. With the flanges 453' positioned beyond the aperture 428 in attachment member 424, tether 422' is pulled proximally relative to tube 450', transitioning the tube 450' and tether 422' assembly to the locked condition, as shown in FIG. 5C. In this locked condition, the flanges 453' are splayed outwardly and at least partially overlie the tether member 426', with the largest diameter of the tube 450' and tether 422' assembly being larger than the diameter of apt' lure 428 such that the tube 450' and tether 422' assembly is unable to be removed from the attachment member 424 via aperture 428.

Figure 6A:
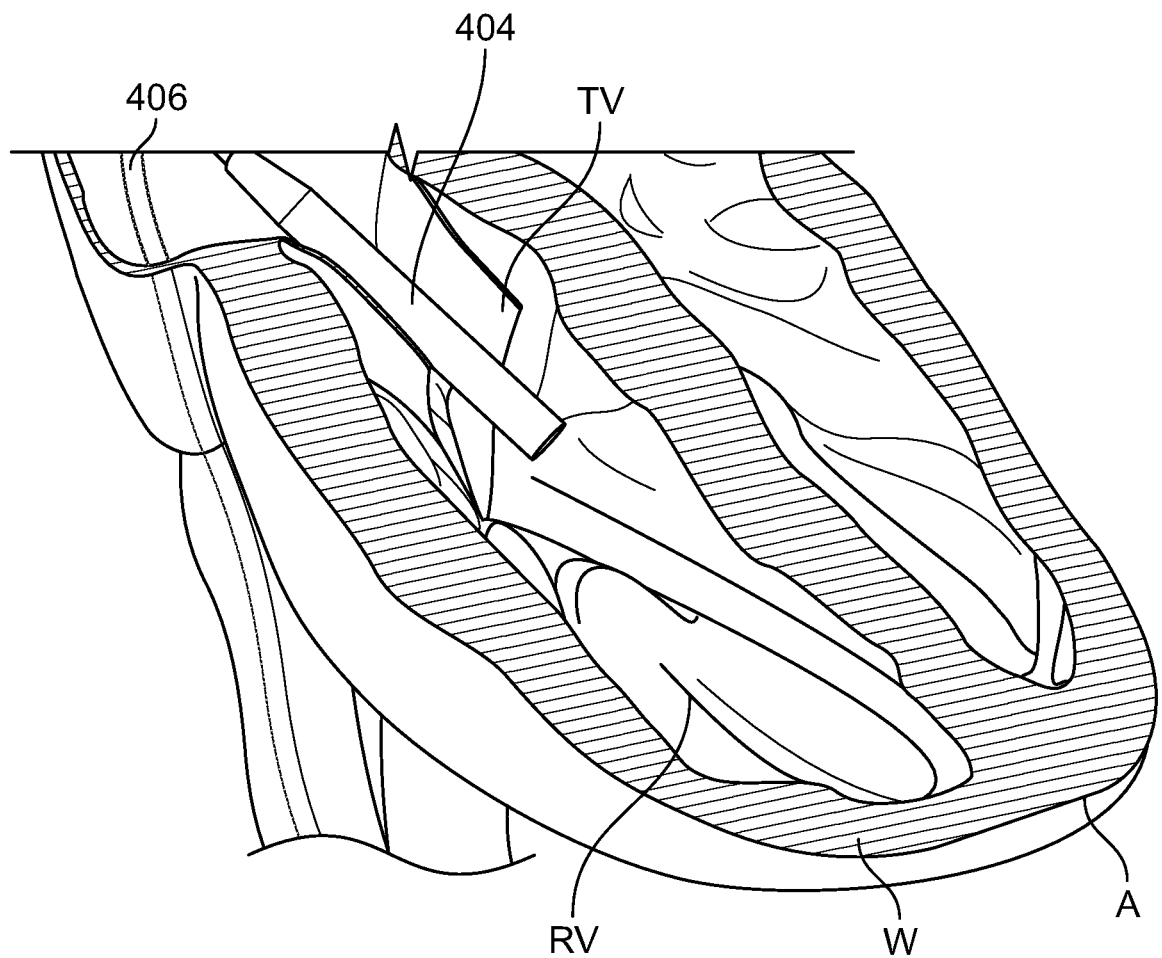
FIGS. 6A-D are schematic views showing a method of implanting an IMD using the delivery catheter of FIG. 4A.
Figure 6B:
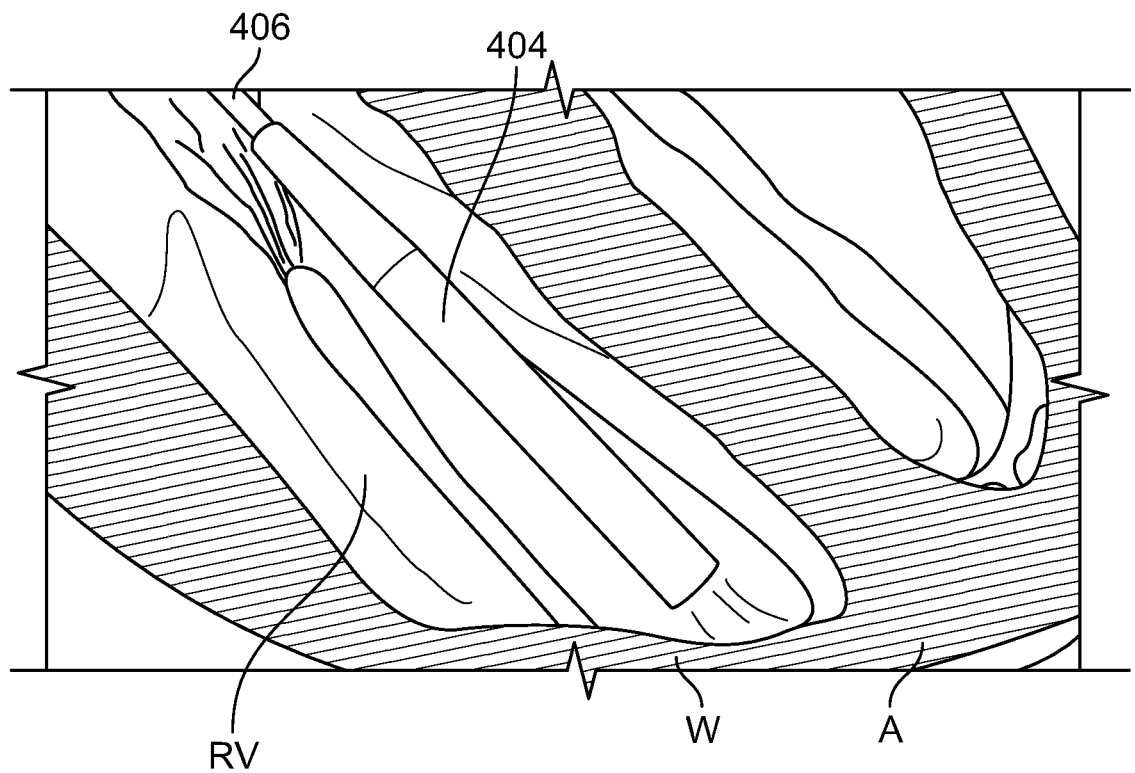

An exemplary use of delivery system 400' to implant an IMD 402 in a patient is described below. In this example, IMD 402 is an implantable pacemaker. Before inserting IMD 402 into the patient's body, tube 450' and tether 422' are assembled together, passed through aperture 428 in the attachment member 424 of the IMD, and transitioned to the locked condition as described above and shown in FIGS. 5A-C. With tube 450' and tether 422' in the locked condition, IMD 402 is prevented from unintentionally detaching from the tube 450' and tether 422' assembly. Once tube 450' and tether 422' are in the locked condition, the delivery catheter 407 may be advanced until the torque key 432 of IMD 402 is engaged in the recess 430 in the docking cap 418. At this point, tether shuttle 112, which may alternatively be referred to as a docking shroud or control knob, may be pulled proximally, resulting in a proximal force applied to tether 422'. This may result in tension being applied on the tether 422', pulling torque key 432 into secure engagement with recess 430. It should be understood that tether 422' may stretch a small degree due to the applied tension. With the torque key 432 engaged in recess 430, IMD sheath 404 may be advanced distally with respect to IMD 402 until the distal end of the IMD sheath surrounds the helix 403 of the IMD. A desired blood vessel, such as the femoral vein, may be accessed using known techniques and the delivery catheter 407 may then be introduced into the femoral vein. The delivery catheter 407 may then be advanced through the vasculature until the distal end of the delivery catheter is near the desired implantation site. For example, the distal end of delivery system 400; including the IMD sheath 404, may be passed through the tricuspid valve TV and into the right ventricle RV, as shown in FIG. 6A. It should be understood that the delivery may be performed while the heart is beating. FIG. 6B shows the IMD sheath 404 positioned adjacent the desired implantation site, which in this example is a portion of the right ventricular wall W near the apex A of the heart.

Figure 6C:
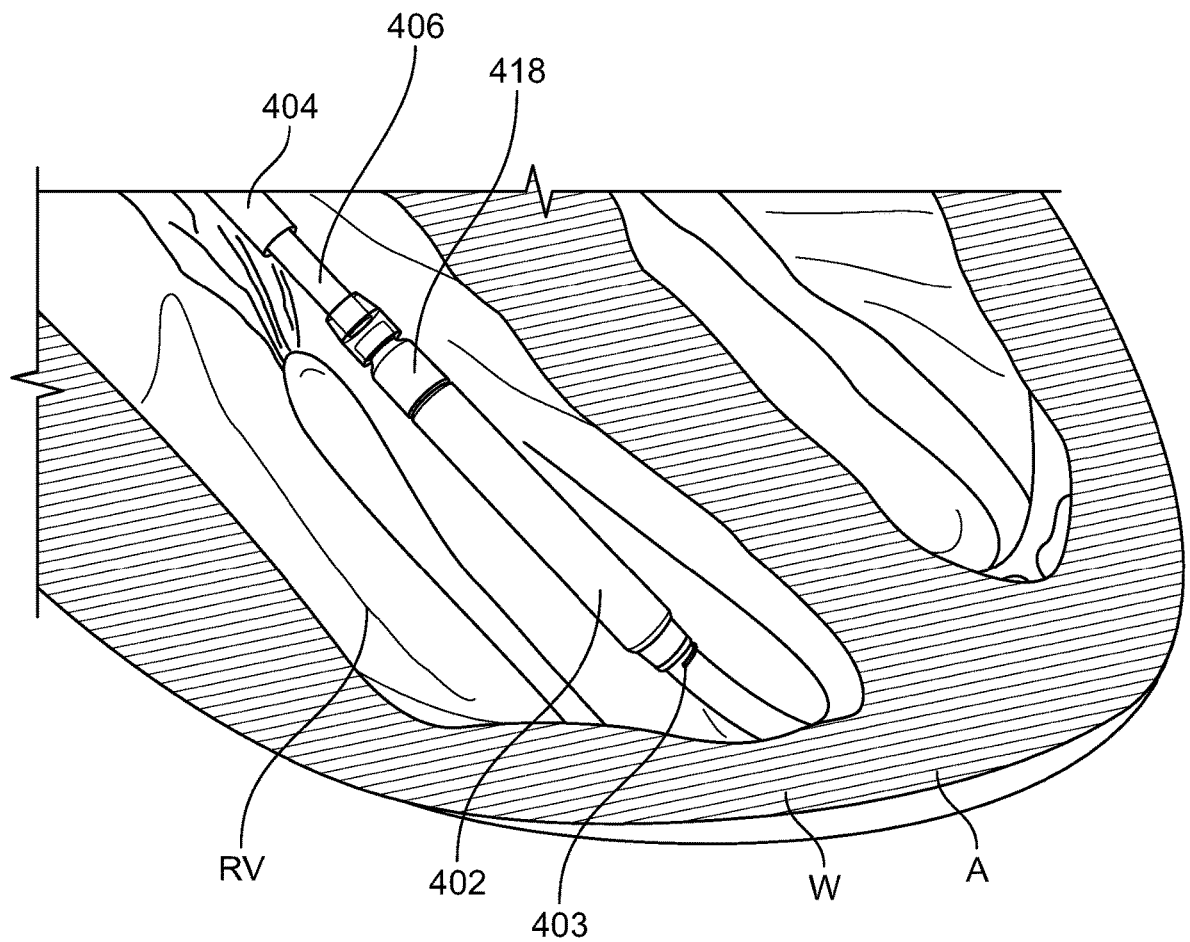
Figure 6D:
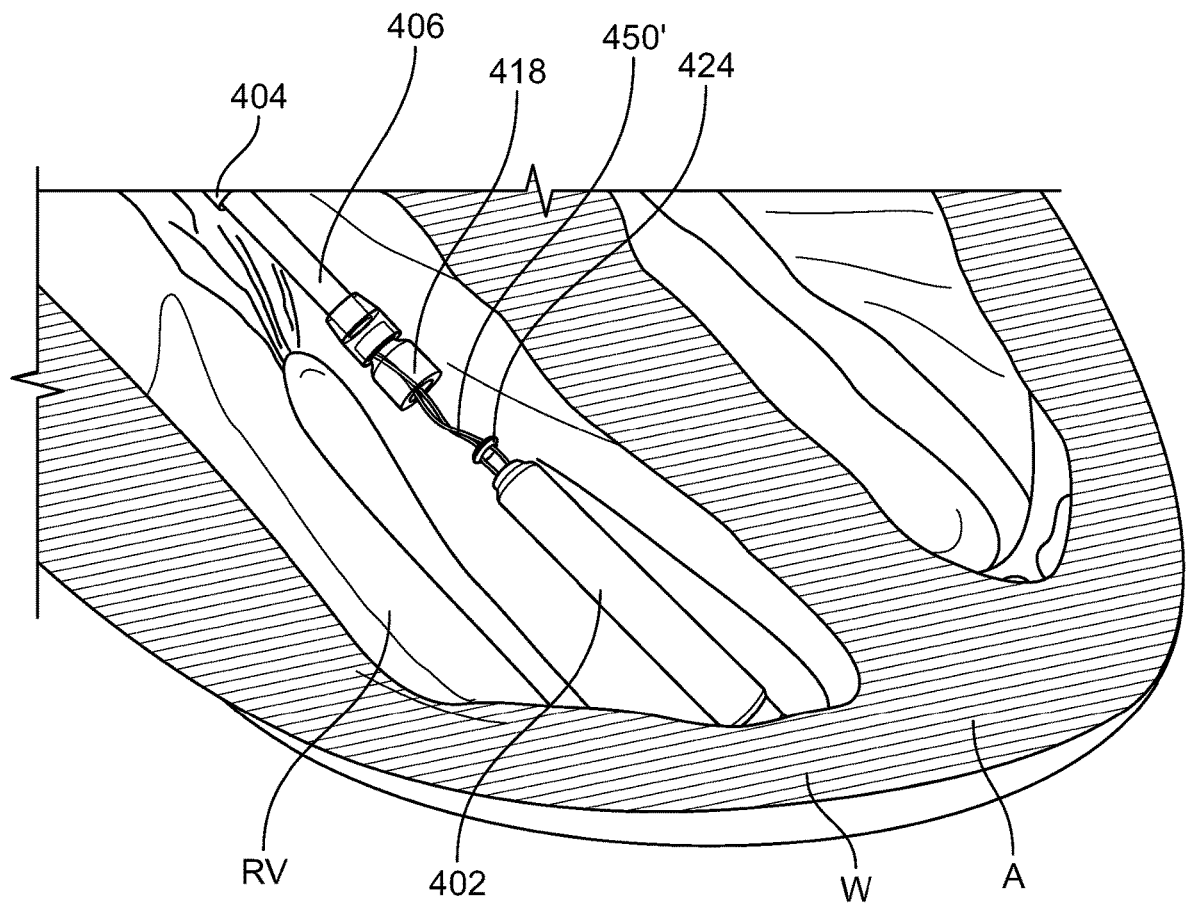

With IMD 402 adjacent the desired implantation site, the IMD sheath 404 may be withdrawn to expose IMD 402 and docking cap 418, as shown in FIG. 6C. The user may advance the exposed IMD 402 until helix 403 contacts the right ventricular wall W, for example by pushing the catheter handle forward or distally. Once contact is made, the user may rotate IMD 402 by rotating docking cap 418 (for example, using an actuator on a handle of delivery system 400'). Docking cap 418 may be rotated, for example, by rotating the torque shaft coupled to the docking cap. The torque shaft may be rotated via rotation of a corresponding control knob on the handle, which may be the same as tether shuttle 112, or may be a separate control knob. It should be understood that bearings may be provided, for example between a proximal end of docking cap 418 and a distal end of catheter shaft 406, to facilitate smooth rotation of the docking cap. Because the torque key 432 of IMD 402 is engaged in the recess 430 in docking cap 418, rotation of the docking cap causes rotation of IMD 402, and corresponding rotation of helix 403. The user continues such rotation until the helix 403 pierces and penetrates the right ventricular wall W, securing IMD 402 to the right ventricular wall W. With the IMD 402 secured to the ventricular tissue, docking cap 418 may be disengaged from IMD 402 and pulled proximally with respect to the IMD, for example by advancing tether shuttle 112 distally to release the tension on tether 422' that was pulling the torque key 432 of the IMD into secure engagement with the docking cap. At this point, as shown in FIG. 6D, the tube 450' and tether 422' assembly is still in the locked condition, and the IMD 402 is still coupled to delivery system 400'. However, the IMD 402 is able to simulate the function it will have when it is no longer coupled to delivery system 400'. For example, because tube 450' and tether 422' are very flexible, the coupling between the tube 450' and tether 422' assembly and the attachment member 424 does not apply any significant forces to IMD 402. Because the heart is beating during the procedure, the implanted IMD 402 may be able to move substantially freely as the heart beats, and the user can determine how the IMD 402 is functioning in this environment. This may include, for example, determining how electrical signals from the IMD 402 are interacting with the beating heart. Had such testing been conducted with docking cap 418 still engaged with IMD 402, the testing may have been less indicative of how the IMD 402 will function once entirely uncoupled from the delivery system 400', as the mechanical connection may have affected such testing.

If testing determines that IMD 402 is functioning in an undesirable manner, the delivery catheter 407 may be advanced to again engage the docking cap 418 with torque key 432. Subsequently, the IMD 402 may be rotated in the opposite direction to disengage helix 403 from the ventricular wall W, and IMD 402 may either be removed from the patient's body or repositioned to a different portion of the ventricular wall W. The reconnection of docking cap 418 with IMD 402 is facilitated by the fact that tube 450' and tether 422' remain coupled to the attachment member 424 of IMD 402 while in the tethered state. Without that attachment, it might be difficult or impossible to re-engage the docking cap 418 with IMD 402.

If testing determines that IMD 402 is functioning in a desired manner, delivery system 400' may be completely disengaged from IMD 402. This may be accomplished by placing tether 422' in the released condition, namely, by advancing tether 422' distally with respect to tube 450' until the distal end of tube 450' surrounds only or substantially only the cylindrical portion 423' of tether 422'. With this relative positioning, the largest diameter of the tube 450' and tether 422' assembly is smaller than the diameter of aperture 428 in attachment member 424. Accordingly, the tube 450' and tether 422' may be pulled proximally together with respect to attachment member 424 until the distal ends of the tube and tether both exit attachment member 424 via aperture 428. The steps to disengage delivery system 400' from IMD 402 are the same as those described above in connection with coupling delivery system 400' to IMD 402, but in reverse order. With the IMD 402 completely detached from the delivery system 400', the delivery device may be removed from the patient's body, with the IMD 402 remaining in place following confirmation of its proper functioning.

Figure 7:
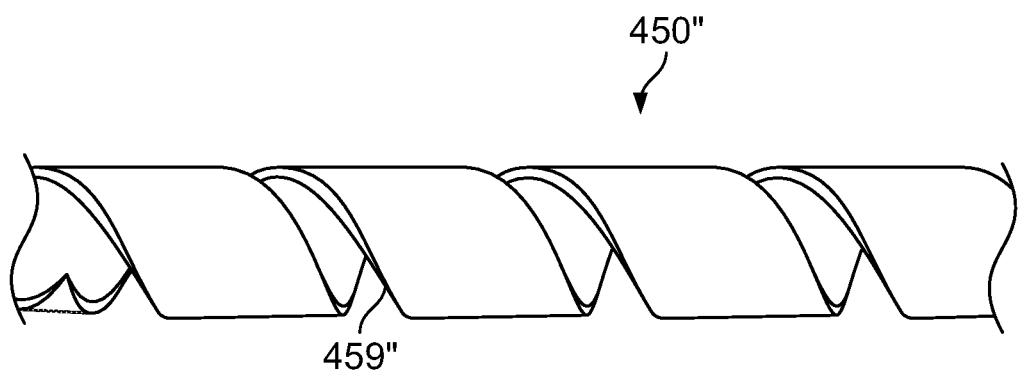
FIG. 7 is a partial side view of the tube of FIG. 4B with modified surface features.

As should be understood from the above, the tether 422' and the tube 450', both individually and in the assembled condition, are preferably flexible enough so that the coupling of tether 422' and tube 450' to IMD 402 does not significantly affect movement of the IMD 402 caused by the beating heart. Preferably, the material and geometry of both tether 422' and tube 450' provide for a high level of flexibility to achieve this goal. However, tube 450' may be modified to increase its flexibility. For example, FIG. 7 illustrates a section of a modified tube 450". The modification may include a laser cut pattern 459" on a distal end portion of tube 450". For example, a spiral pattern may be laser cut in the outer surface of the distal end portion of tube 450", such that the cut extends through the wall of tube 450" in a spiral pattern 459". The end result may be a tube 450" with the general shape of a spiraled ribbon. However, in other embodiments, the spiral cut may not extend completely through the wall of the tube, but rather merely reduce the wall thickness in a spiral pattern to provide increased flexibility. It should be understood that other modifications may be made, including other types of laser cut patterns, to increase the flexibility of tube 450'. It should also be understood that any such modification, such as spiral pattern 459", may be limited to the distal end portion of tube 450" that protrudes from docking cap 418 when delivery system 400' is in the tethered state with IMD 402.

Although IMD 402 is described in the above examples as an implantable pacemaker, IMD 402 may be any one of various types of implantable devices, such as, for example, an implantable cardioverter-defibrillator ("ICD"), defibrillator, cardiac rhythm management ("CRM") device (such as a pacemaker), neurostimulator, or the like. When taking the form of a pacemaker, IMD 402 may include a leadless cardiac pacemaker that may be enclosed in a hermetic housing or that may be positioned on the inside or outside of a cardiac chamber. The pacemaker may have two or more electrodes located within, on, or near the housing for delivering pacing pulses to muscle of the cardiac chamber and optionally for sensing electrical activity from the muscle, and for bidirectional communication with at least one other device within or outside the body. The housing may contain a primary battery providing power for pacing, sensing, and communication, for example bidirectional communication. The housing may optionally contain circuits for sensing cardiac activity from the electrodes, for receiving information from at least one other device via the electrodes, and/or for generating pacing pulses for delivery via the electrodes. The housing also may optionally contain circuits for transmitting information to at least one other device via the electrodes and/or circuits for monitoring device health. The housing may contain circuits for controlling these operations in a predetermined manner. However, it should be understood that the tethering system of delivery system 400' may be used with other implantable devices other than cardiac pacemakers where it is desired to have the option of a tethered state between the delivery device and the implantable device.

According to one aspect of the disclosure, a delivery system is for delivering an implantable medical device having an aperture with a first diameter, and the delivery system comprises:

a catheter shaft having a distal end;

a tube disposed within the catheter shaft and having a main portion with a second diameter, a distal end and an expandable distal end portion extending distally beyond the distal end of the catheter shaft; and a tether disposed within the tube, the tether including an elongated body having a distal end and a tether member at the distal end of the body, the tether member having a third diameter greater than the second diameter and smaller than the first diameter, the tether being slideable relative to the tube from a released condition in which the tether member is positioned at least partially distal to the distal end of the tube, and a locked condition in which the tether member is at least partially surrounded by the expandable distal end portion of the tube, wherein in the released condition, the distal end of the tube has a diameter smaller than the first diameter, and in the locked condition, the distal end of the tube has a diameter larger than the first diameter; and/or the tether member increases in diameter in a proximal-to-distal direction; and/or the tether member includes a conical or frustoconical portion; and/or the tube extends in a longitudinal direction, and the distal end of the tube includes a plurality of slots oriented parallel to the longitudinal direction; and/or each slot extends proximally from the distal end of the tube; and/or the plurality of slots are spaced at equal intervals around a circumference of the tube; and/or the plurality of slots includes four slots; and/or the distal end portion of the tube is integral with the main portion of the tube; and/or the diameter of the distal end of the tube in the released condition is equal to the second diameter; and/or a pattern is produced in an outer surface of the main portion of the tube, the main portion of the tube having a first wall thickness in areas having the pattern and the main portion of the tube pattern having a second wall thickness greater than the first wall thickness in areas without the pattern; and/or the pattern comprises a spiral; and/or the tube is for lied of a shape memory material; and/or the tube is formed of a nickel-titanium alloy; and/or the distal end of the tube in the released condition has a diameter equal to the second diameter; and/or a sheath is advanceable from a first position that does not surround the medical device to a second position that surrounds the medical device.

Another aspect of the disclosure is directed to a method of implanting a medical device in a patient, the medical device having an aperture with a first diameter, and the method comprises:

providing a delivery device having a catheter shaft with a distal end, a tube disposed within the catheter shaft, and a tether disposed within the tube;

advancing the tube and tether distally through the aperture while the tube is in a released condition in which a distal end of the tube has a diameter smaller than the first diameter;

retracting the tether proximally relative to the tube to transition the tube to a locked condition in which the distal end of the tube has a diameter larger than the first diameter;

provisionally implanting the medical device into the patient while the tube is in the locked condition; and removing the delivery device from the patient; and/or evaluating a function of the medical device after the provisional implanting step and prior to the removing step; and/or advancing the tether distally relative to the tube to transition the tube back to the released condition after evaluating the function of the medical device; and/or removing the tube and the tether from the aperture after transitioning the tube back to the released condition; and/or the step of removing the delivery device from the patient includes removing the medical device from the patient after the evaluating step and while the tube is in the locked condition.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A delivery system for delivering an implantable medical device having an aperture with a first diameter, the delivery system comprising:
 a catheter shaft having a distal end;
 a tube disposed within the catheter shaft and having a main portion with a second diameter, a distal end and an expandable distal end portion extending distally beyond the distal end of the catheter shaft; and
 a tether disposed within the tube, the tether including an elongated body having a distal end and a tether member at the distal end of the body, the tether member having a third diameter greater than the second diameter and smaller than the first diameter, the tether being slideable relative to the tube from a released condition in which the tether member is positioned at least partially distal to the distal end of the tube, and a locked condition in which the tether member is at least partially surrounded by the expandable distal end portion of the tube,
 wherein in the released condition, the distal end of the tube has a diameter smaller than the first diameter, and in the locked condition, the distal end of the tube has a diameter larger than the first diameter.

2. The system of claim 1, wherein the tether member increases in diameter in a proximal-to-distal direction.

3. The system of claim 2, wherein the tether member includes a conical or frustoconical portion.

4. The system of claim 1, wherein the tube extends in a longitudinal direction, and the distal end of the tube includes a plurality of slots oriented parallel to the longitudinal direction.

5. The system of claim 4, wherein each slot extends proximally from the distal end of the tube.

6. The system of claim 4, wherein the plurality of slots are spaced at equal intervals around a circumference of the tube.

7. The system of claim 4, wherein the plurality of slots includes four slots.

8. The system of claim 1, wherein the distal end portion of the tube is integral with the main portion of the tube.

9. The system of claim 1, wherein the diameter of the distal end of the tube in the released condition is equal to the second diameter.

10. The system of claim 1, wherein a pattern is produced in an outer surface of the main portion of the tube, the main portion of the tube having a first wall thickness in areas having the pattern and the main portion of the tube pattern having a second wall thickness greater than the first wall thickness in areas without the pattern.

11. The system of claim 10, wherein the pattern comprises a spiral.

12. The system of claim 11, wherein the distal end of the tube in the released condition has a diameter equal to the second diameter.

13. The system of claim 1, wherein the tube is formed of a shape memory material.

14. The system of claim 13, wherein the tube is formed of a nickel-titanium alloy.

15. The system of claim 1, further comprising a sheath advanceable from a first position that does not surround the medical device to a second position that surrounds the medical device.

16. A method of implanting a medical device in a patient, the medical device having an aperture with a first diameter, the method comprising:
 providing a delivery device having a catheter shaft with a distal end, a tube disposed within the catheter shaft, and a tether disposed within the tube;
 advancing the tube and tether distally through the aperture while the tube is in a released condition in which a distal end of the tube has a diameter smaller than the first diameter;
 retracting the tether proximally relative to the tube to transition the tube to a locked condition in which the distal end of the tube has a diameter larger than the first diameter;
 provisionally implanting the medical device into the patient while the tube is in the locked condition; and
 removing the delivery device from the patient.

17. The method of claim 16, further comprising evaluating a function of the medical device after the provisional implanting step and prior to the removing step.

18. The method of claim 17, further comprising advancing the tether distally relative to the tube to transition the tube back to the released condition after evaluating the function of the medical device.

19. The method of claim 18, further comprising removing the tube and the tether from the aperture after transitioning the tube back to the released condition.

20. The method of claim 17, wherein the step of removing the delivery device from the patient includes removing the medical device from the patient after the evaluating step and while the tube is in the locked condition.

\* \* \* \* \*